(12) United States Patent
Ramberg

(10) Patent No.: US 6,709,829 B2
(45) Date of Patent: Mar. 23, 2004

(54) METHODS AND COMPOSITIONS FOR DETECTION OF DISEASE

(75) Inventor: Elliot R. Ramberg, Del Ray Beach, FL (US)

(73) Assignee: Cygene, Inc., Coral Springs, FL (US)

( * ) Notice: Subject to any disclaimer, the term of this patent is extended or adjusted under 35 U.S.C. 154(b) by 0 days.

(21) Appl. No.: 09/776,568

(22) Filed: Feb. 2, 2001

(65) Prior Publication Data

US 2003/0022256 A1 Jan. 30, 2003

Related U.S. Application Data

(60) Provisional application No. 60/179,668, filed on Feb. 2, 2000, provisional application No. 60/183,377, filed on Feb. 18, 2000, and provisional application No. 60/218,879, filed on Jul. 18, 2000.

(51) Int. Cl.⁷ .................... G01N 33/53; C12Q 1/68; C12P 19/34; A61K 39/395; A61K 39/00
(52) U.S. Cl. .................... 435/7.1; 435/6; 435/91.1; 424/130.1; 424/178.1; 424/184.1
(58) Field of Search .................. 435/7.1, 183; 436/501; 424/130.1, 136.1, 137.1, 138.1, 184.1, 193.1, 194.1, 195.1

(56) References Cited

U.S. PATENT DOCUMENTS

| | | |
|---|---|---|
| 4,642,284 A | 2/1987 | Cooper et al. |
| 4,810,631 A | 3/1989 | Perlman et al. |
| 5,804,370 A | 9/1998 | Romaschin et al. |

OTHER PUBLICATIONS

Juhl et al., A monoclonal antibody–Cobra venom factor conjugate increases the tumor–specific uptake of a 99mTc–labeled anti–carcinoembryonic antigen antibody by a two step approach. Cancer Research, 55, 5749s–5755, Dec. 1, 1995.*

Jeffrey C. Edberg et al., "Quantitative Analysis of the Relationship Between c# Consumption, C3b Capture, and Immune Adherence of Complement–Fixing Antibody/DNA Immune Complexes", Journal of Immunology, vol. 141, No, 12, Dec. 15, 1988, pp 4258–4265.

* cited by examiner

Primary Examiner—Ethan Whisenant
Assistant Examiner—Frank Wei Min Lu
(74) Attorney, Agent, or Firm—Buchanan Ingersoll PC

(57) ABSTRACT

The present invention is directed to methods and compositions for detection of target analytes, comprising proteins and nucleic acids, in multiple cellular compartments. Preferred embodiments comprise the use of complement-mediated assays. Methods and compositions for monitoring multiple stages of disease and infection are presented.

12 Claims, 7 Drawing Sheets

METHODS AND COMPOSITIONS FOR DETECTION OF DISEASE

RELATED APPLICATIONS

Figure 1:
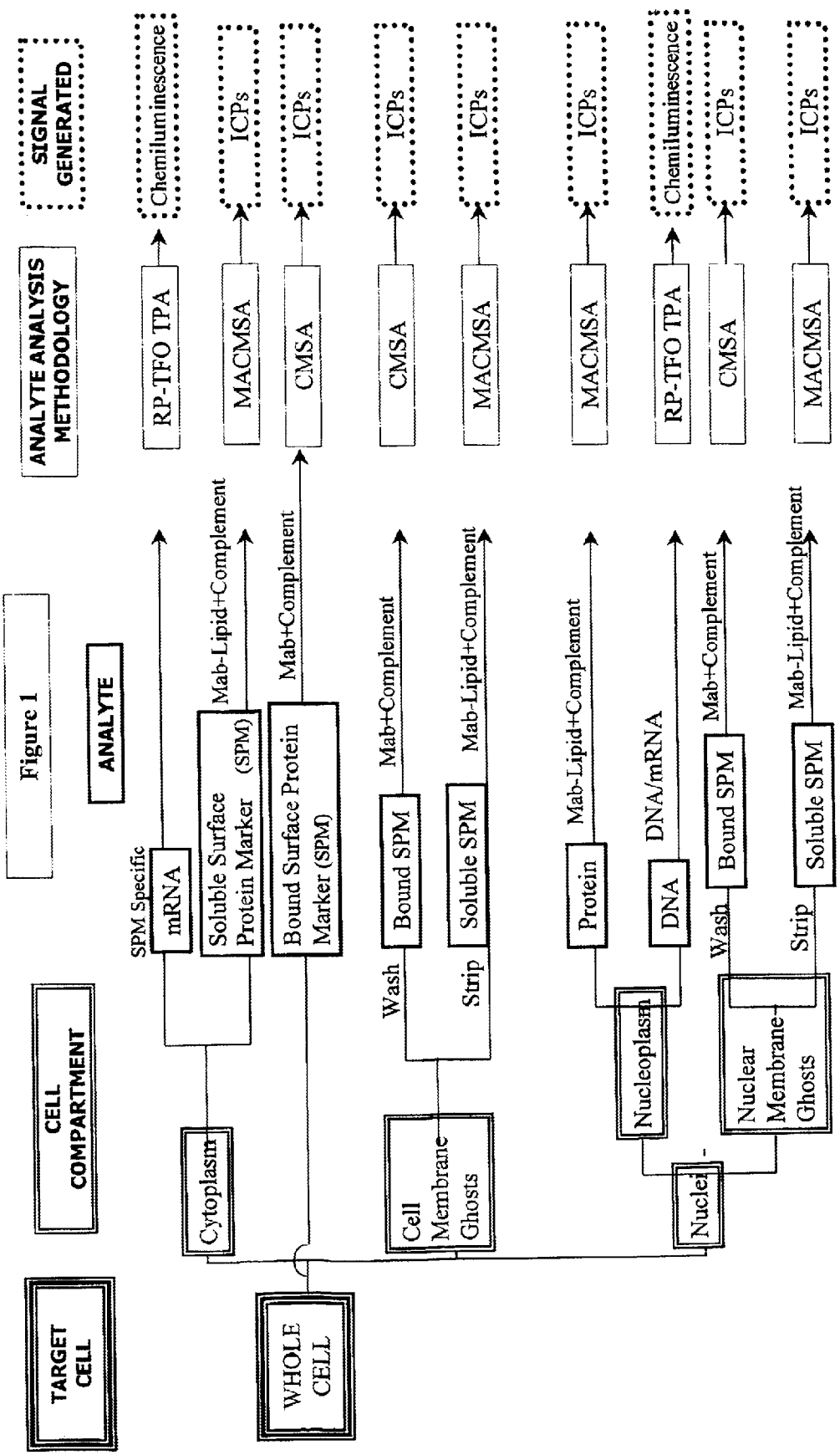
Figure 2:
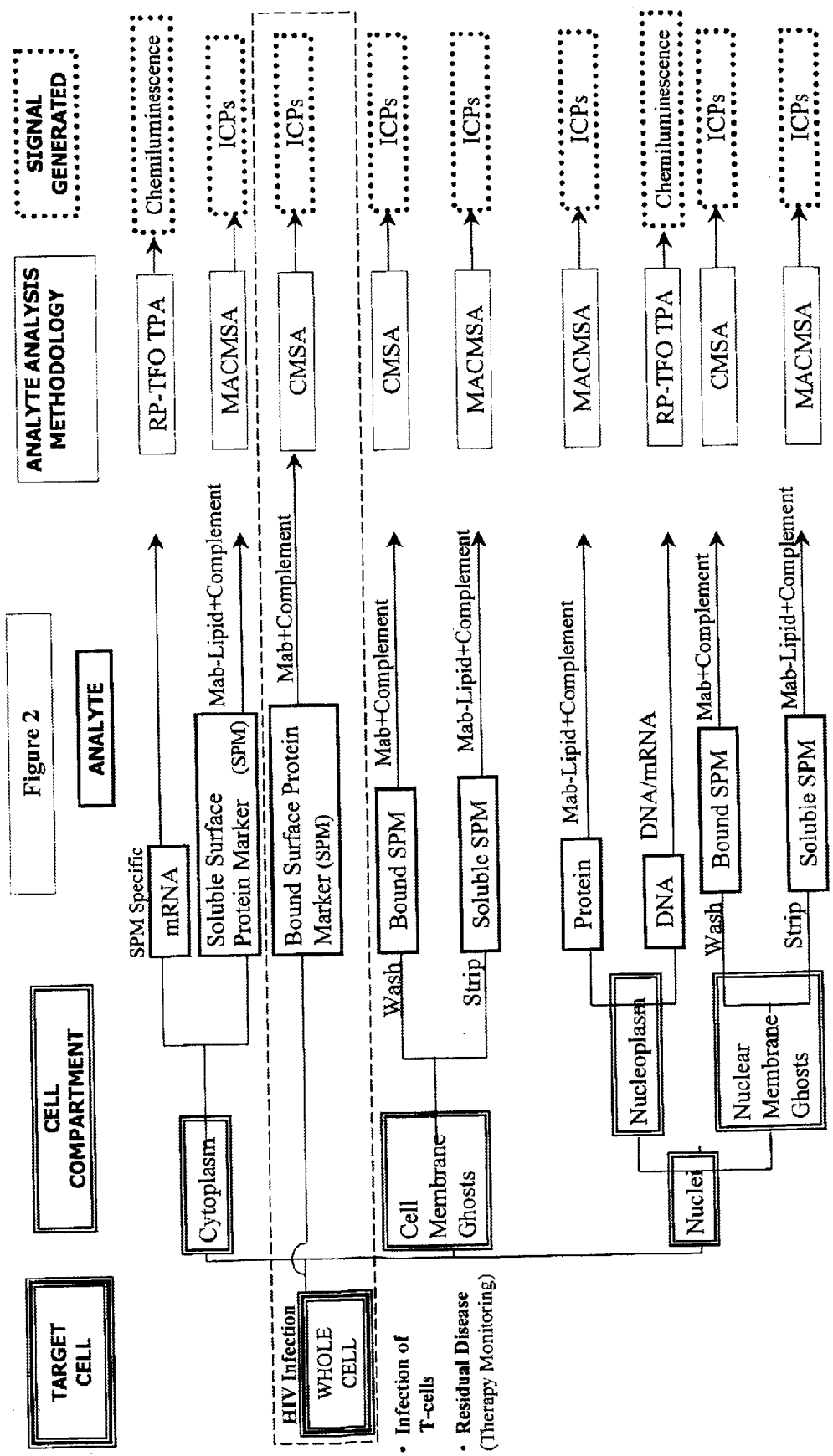
Figure 3:
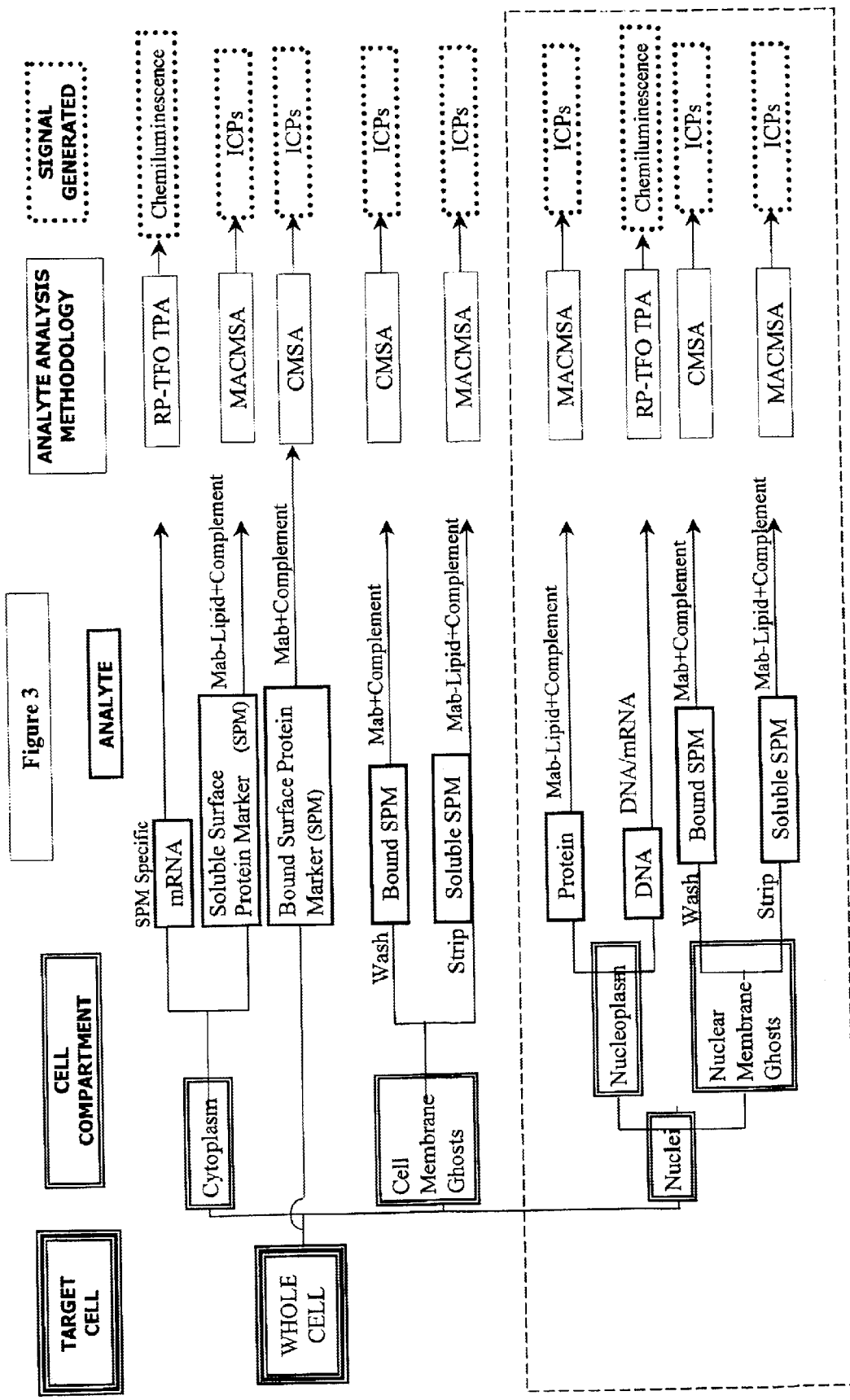

This application claims priority to U.S. Provisional Patent Application Nos. 60/179,668, filed Feb. 2, 2000, 60/183,377, filed Feb. 18, 2000, and 60/218,879, filed Jul. 18, 2000, all of which are herein incorporated in their entireties.

FIELD OF THE INVENTION

The present invention is directed to methods and compositions for detecting pathological conditions. In particular, the invention comprises methods and compositions using biological factors, such as complement components, for detecting pathological conditions.

BACKGROUND OF THE INVENTION

Diagnostics has traversed a broad range of disciplines from an initial foothold in serologic diagnostics to DNA molecular diagnostics, such as those using PCR. Problems with many current diagnostic technologies include the inability to directly detect species specific mRNA and proteins, and many also lack specificity and sensitivity. The problems of detection of molecular cancer metastasis, detection of residual disease, the early detection of HIV and other viral agents, sensitive carcinogen detection, sensitivity in detection of pathologic proteins or cells in normal tissue, and the need for heightened specificity and sensitivity in the determination of the precancerous state of dysplasia, illustrate the need for more accurate, sensitive and specific assays. Furthermore, most of these assays fail in detection of very low numbers of antigen or analyte targets, such as low number DNA, mRNA, protein or cellular targets in the presence of a large amount of non-specific material such as genomic DNA, mRNA, protein, or cells.

One example of a diagnostic test that has been shown to be inaccurate at a rate higher than wanted is the Papanicolau Cervical Screen (PAP test), developed in 1924 by George N. Papanicolau and Aureli Babes. Koss (1989) reviewed this diagnostic test and concluded that "although this cancer detection system (PAP test) has been shown to be effective in reducing the state of morbidity and mortality from invasive cervical cancer in appropriately screened populations, there is no evidence that the PAP test has succeeded anywhere in complete eradication of this theoretically preventable disease." The test is based on the theory that pre-cancerous changes still confined to the epithelium of the uterine cervix (carcinoma in situ) could be identified in exfoliative cytologic specimens. On the assumption that the early detection of these pre-cancerous lesions would prevent invasive cancer of the uterine cervix, the test became a widely used test cancer detection and prevention. The test is based upon a labor-intensive complex process, and the outcome depends entirely on human judgment, variable standard at best. What is needed are improvements to the currently used PAP smear.

A major obstacle in an exfoliative cell diagnostic screening test such as the PAP test is the identification, of cells that reflect abnormal cancerous or pre-cancerous changes in the surface epithelium among the multitude of the cells present. Recent FDA regulatory trends have approved the placement of fewer exfoliative cells on the slide to be stained and scored to allow ease of scoring. Paradoxically, this limitation of exfoliative cell numbers results in diminished test sensitivity and false negative results. Currently 30,000 exfoliative cells are scored on a PAP smear. This reduction in cellular sample size decreases the sensitivity of the assay. A better designed diagnostic process would be required to score millions of exfoliative cells with high specificity and sensitivity.

Interpretation of test results possesses a similar dilemma for analysis of cellular smears due to the fact that smears do not always reflect underlying diseases. In the case of invasive cancer, the surface of the lesions is often necrotic and covered by debris resulting in an inability for the smear to reveal obvious cancer cells. The best determinative test involves a careful clinical examination with biopsy of any visual suspicious cervical lesion and additionally, many pre-cancerous and cancerous lesions may be represented in a cellular smear sample by only a few cells with relatively trivial abnormalities. Determination of the presence of dysplasia is also complicated because not all neoplastic cervical lesions shed cells in a uniform fashion and some lesions are difficult to sample.

The principal goal of cervical smear scoring is to not diagnose overt clinical disease, but to detect occult small carcinomas and pre-cancerous abnormalities that may lead to invasive cancer. To achieve this, the diagnostic screen must be sensitive enough to detect low copy number cells of interest, precancerous and occult cancer. The function of the dysplasia screen is to signal the presence of cellular abnormalities and refer the individual for further follow-up. Repeated tests may not result in the same diagnosis and neoplastic conditions may pass undetected. A more valid approach for detection of the presence of dysplasia/neoplasia would be based on multiple factorial assays performed in concert. This includes inspection of the exfoliative sample on the nuclear level, the cell surface level, and the cytoplasmic level to confirm detection of disease.

Other examples of diagnostic assays lacking sensitivity include the HIV assays currently in use. These assays generally do not detect the stage of the disease in the patient because of an inability to detect low copy number targets early in HIV infection. Many of these assays detect seroconversion at approximately 6 months post infection. The assay is based upon one biological response, such as antibody production in response to the virus. A better assay would be one that measured both cellular and molecular biological responses, such as nucleic acid and protein measurements, and detection of cell surface antigens.

Currently, HIV diagnostic tests are configured to identify a large number of viral proteins present in a sample, and the presence of a large-scale antibody produced by the body to the virus. Earlier diagnosis would be invaluable for treatment of the infected persons. Furthermore, DNA diagnostic processes, using PCR, are limited to a small size sample compromises the sensitivity of the diagnostic test. What is needed are improvements in current diagnostic testing for HIV that can detect the infection early in its time-course with a high level of sensitivity that will also permit monitoring of residual disease during therapy of the HIV infected patient.

Other sensitive assays that are needed include those capable of detecting low levels of carcinogens and other harmful compounds, such as Aflatoxin B1 as well as the other polycylic aromatic hydrocarbons (PAHs). Currently, Aflatoxin B1 detection assays are sensitive to a level of parts per billion. This and other carcinogens may form DNA adducts in germ cells as their mechanism of action, and thus even a very few molecules may exert a carcinogenic effect and are undetectable with current tests. Exposure to the Aflatoxin B1 containing material carries increased risk for carcinogenesis in the consumer. What is needed is a diagnostic technology that will possess sensitivity below parts per billion.

Other attempts at measuring infectious agents include the tests for prions. Creutzfeld-Jakob disease (CJD) of humans and bovine spongiform encephalitis (BSE) and scrapie of animals are neurodegenerative diseases caused by prion proteins. The infectious prion is an abnormal disease-producing isoform of the normal prion protein (PrP) called $PrP^{sc}$. Brain damage in prion disease occurs when abnormal prion protein molecules, as a consequence of ingestion gain entry to the brain and cause normal PrPs to take on the disease causing $PrP^{sc}$ form.

Currently a labeled mouse monoclonal antibody 3F4 has been shown to bind prions with a sensitivity of binding of the antibody of 5 picograms per ml. This indicates that billions of prion protein molecules or greater would be necessary to be present to support detection of binding of the antibody to the aberrant prion. Furthermore, the assay is complex, requiring selective precipitation of $PrP^{sc}$ by sodium phosphotungstate. This inability to more sensitively detect the presence of the prions in TSEs has hampered an understanding of the disease, attempts to determine if a cure scenario is feasible, and development of a vaccine.

What is needed are methods and compositions that will detect the protein in a large sample of plasma and concentrate and collect the normal and the aberrant forms of the prion in a small volume. Furthermore, methods are needed for diagnostic assays that will detect the presence of the aberrant prion protein with high levels of sensitivity.

What is needed are methods and compositions that recognize the presence of very low numbers of infectious or other targets in an excess of non-specific, non-target or normal material. The target may be nucleic acid, such as DNA and RNA, cellular, or protein, in nature. Ideally, these methods and compositions comprise diagnostic technology that supports high levels of specificity and sensitivity in testing procedures. Preferred methods and compositions comprise diagnostic tests that are configured for early detection of the pathologic agent or other target in the sample by examining the DNA, RNA, cell, or soluble protein in solution, to detect the pathologic target earlier in the infection time-course.

SUMMARY OF THE INVENTION

The present invention is directed to methods and compositions for detecting pathological conditions. In particular, the invention comprises methods and compositions using biological factors, such as complement components, for detecting pathological conditions. Particularly described are assays for non-specific target elimination that allow for detection of low copy number targets in a large field of nontarget material. Such assays comprise methods comprising CMSA and MACMSA, which preferably comprise detection of complement proteins and components. The assays of the present invention can be used for detection of changes in cellular molecules or nucleic acids that are part of disease states or infections, or can be used for detection of molecules in the environment.

Not only do the methods and compositions of the present invention comprise detection of nucleic acid and other molecular targets, but the methods and compositions of the present invention comprise diagnostics at supramolecular levels to confirm the presence of the pathologic or other cellular targets in tissues. The present invention comprises the analysis of only the cell subset of interest in a very large cell specimen and has the ability to compartmentalize and assay each cell component for the analyte of interest. Other embodiments comprise target analyte sorting and separation from non-specific analyte for increased sensitivity of detection. CMSA comprises the fixation and activation of complement by interactions between cell subset specific surface membrane proteins, and monoclonal or other antibodies. The initiation of the complement fixation process results in the production of the C3a peptide in quantities directly proportional to the extent of complement fixation.

One embodiment of CMSA, called MACMSA, comprises use of a soluble immunogen found in the cytoplasm or released into the cellular environment. These methods and compositions are used to diagnose the presence of pathologic or other specific soluble immunogens in the cytosol or those released into the surrounding media. The diagnostic assays of the present invention are able to accurately diagnose the presence of the disease state and also determine the position of the patient in the time-course of the disease or other process.

DESCRIPTION OF THE FIGURES

FIG. 1 shows an embodiment of the present invention for analyzing a normal cell mass for a low copy number pathogenic or other cell subset target cel, and the processing of the cells' unit parts in order to confirm the diagnostic result.

FIG. 2 shows an embodiment of the present invention for analyzing a normal cell mass for a low copy number of infected target cells, and the processing of the pathogenic cells' unit parts in order to confirm the diagnostic result.

FIG. 3 represents a method of analyzing a normal cell mass for a low copy number pre-cancerous, dysplastic target cells, and the processing of the abnormal cells' unit parts in order to confirm the diagnostic result.

FIG. 4 represents the method of analyzing a normal cell mass for a low copy number cancerous target cell, and the processing of the cells' unit parts in order to confirm the diagnostic result.

FIGS. 5A & 5B represents an example of the Dysplasia/Cancer Screen including complement mediated signal amplification.

FIG. 6 represents another embodiment for the robotic processing of the exfoliative cell specimens.

Table I represents the stoichiometry of C3a peptide production by fixation and activation of complement by the classical pathway.

Table II represents the appearance of nuclear membrane dysplasia markers during the time-course of cervical cancer based on immunohistochemical staining of cervical tissues.

Table III represents the appearance of cell surface membrane dysplasia markers during the time-course of cervical cancer, based on immunohistochemical staining of cervical tissues.

Table IV represents the appearance of cytoplasmic dysplasia markers during the time-course of cervical cancer based on immunohistochemical staining of cervical tissues.

Table V represents the appearance of cellular and transcriptional markers during the time-course of cervical cancer.

Table VI represents the strategies employed to provide an ultra-sensitive multi-parameter test for the presence of microbes producing mycotoxins and the soluble mycotoxins themselves during tobacco processing.

Table VII represents the consensus opinion of the HIV infectious time-course.

Table VIII represents the markers induced by HIV infection and their location during all stages of the HIV infectious time-course.

DETAILED DESCRIPTION

The present invention comprises methods and compositions for the detection of low copy number targets of interest in diagnostic specimens in the presence of a large excess of normal material. The present invention can be used for diagnostic tests and has the capability to analyze specimens at the molecular, cellular, and tissue levels.

Methods and compositions of the present invention comprise non-specific target elimination, NTE. NTE is used with processes that detect pathologic or other targets and supports high limits of specificity and sensitivity. Embodiments of NTE include the Haystack Processing technologies such as TPA (Target Protection Assay), RFTA (Restriction Fragment Target Assay), EAD (Enzyme Assisted Diagnostics) and CPA (Cutter Probe Assays), as described in U.S. Pat. Nos. 5,962,225, 6,100,040, and U.S. patent application Ser. No. 09/633,848, filed Aug. 7, 2000, now U.S. Pat. No. 6,458,540, PCT Application No. PCT/US98/24226, U.S. patent application Ser. Nos. 09/569,504, 09/443,633, and PCT Application No. PCT/US99/27525, each of which is incorporated herein in its entirety. The present invention is directed to methods and compositions including NTE which comprise Selective Target Monitoring technologies (STM) with Complement Mediated Signal Amplification (CMSA) and MACMSA (Membrane Associated Complement Mediated Signal Amplification).

Not only do the methods and compositions of the present invention comprise detection of nucleic acid and other molecular targets, but the methods and compositions of the present invention comprise diagnostics at supramolecular levels to confirm the presence of the pathologic or other cellular target in tissues. STM functions on a cellular or nuclear level to negate the presence of normal cells or nuclei in the sample by the analysis of only the cell subset of interest in a very large cell specimen and has the ability to compartmentalize and assay each cell component for the analyte of interest. These low copy number analytes are detected at low copy numbers by generating a signal from the specific analyte of interest, while no signal occurs from the normal or non-specific analytes present in the compartment. Other embodiments of STM comprise target analyte sorting and separation from non-specific analyte for increased sensitivity of detection.

STM on a cellular level comprises CMSA. CMSA comprises the fixation and activation of complement by interactions between cell subset specific surface membrane proteins, and monoclonal or other antibodies. The initiation of the complement fixation process results in the production of the C3a peptide in quantities directly proportional to the extent of complement fixation.

CMSA is used for detection of target cells and supports NTE in any sample, particularly biological samples including, but not limited to, all body fluids, disaggregated cells, such as those derived from tissue samples, lymph nodes and fine needle aspirates, and environmental samples. An embodiment of CMSA analysis on a cellular level is shown in FIGS. 1 to 6. Herein, the intact cell, or cell membrane ghost, or nucleus is treated with a monoclonal antibody specific for a surface protein of interest, thereby forming an Ab/Ag complex that fixes complement. In the presence of all the complement components, complement is activated to produce C3a peptides, whose quantity is directly proportional to the number of target cells present. The target analyte comprises any cell subset (FIG. 1), an HIV infected T-cell (FIG. 2), a dysplastic cell (FIGS. 3, 5, 6), and a neoplastic cell (FIG. 4) or may also be a cell membrane or cell nucleus, as well as an immunogenic carcinogen or pathologic prion protein molecule.

C3a peptides are produced due to the interactive presence of a lipid membrane containing a unique surface protein (immunogen), a monoclonal or polyclonal antibody, and the complement cascade components. The presence and quantification of the C3a peptide produced may be achieved by any number of methods known to those skilled in the art and discussed herein or in related documents. The key to CMSA is the presence of a lipid membrane that functions to amplify production of the C3a peptide by the complement cascade components. The present invention contemplates the use of lipid membranes found within the sample or lipid membranes that are added to the sample.

The methods and compositions comprising Membrane Associated Complement Mediated Signal Amplification (MACMSA) are used to for sensitive soluble protein analysis. In an embodiment of this method, RBC sensitized stroma, comprising antibody to the unique protein attached to a RBC lipid membrane, interacts with the target analyte molecules present in the sample. Presence of the specific target analyte causes an Ag/Ab reaction to occur at the surface of the lipid RBC membrane, which in the presence of the complement components results in the full amplification of C3a peptide production and sensitive confirmation of the presence of the immunogenic target analyte. MACMSA is capable of molecular confirmation of a cellular diagnostic result as depicted in FIGS. 1 to 6.

Soluble protein or peptide targets or other immunogenic molecules, whether pathologic or not, can be analyzed by STM on a soluble cytoplasmic molecular level that is monitored by use of MACMSA. MACMSA can also sensitively detect protein/peptide targets in any body fluid or other liquid sample. Another function of MACMSA is to detect and monitor non-protein chemicals in solution that are immunogenic thereby fixing and activating complement via the classical pathway, and to detect and monitor polysaccharides or other related molecules that fix and activate complement via the alternative pathway. MACMSA is used for detection of soluble target molecules in any biological or environmental fluid sample including, but not limited to, all body fluids, any soluble protein fluid suspension, environmental fluids, and chemical and material processing fluids containing the soluble, immunogenic target analyte.

Unique pathologic proteins or other immunogens at low molecule number in a vast excess of normal proteins are identified, using STM with high specificity and sensitivity. The specificity comes from the use of multiple specificity steps, and the sensitivity is supported by the minimization of signal background by non-specific target elimination in the fluid samples, either extracellular or intracellular, and generation of signal from all target molecules either intracellular or of exogenous target in a large sample of analyte.

Another embodiment of NTE utilizes STM to selectively capture the analyte subset of interest, such as cells. These cells are then selectively lysed, and their compartments are analyzed for the presence of cell surface disease markers as well as molecular or other cytoplasmic markers to confirm the diagnostic results. Nucleic acids can also be analyzed with high sensitivity using the CMSA and MACMSA processes. STM selectively negates the effect of the contents of non-specific normal cells and their nucleic acid or protein content on the diagnostic assay. This embodiment is referred to as enzymeless selective target monitoring (ESTM) and achieves results similar to EAD (Enzyme Assisted Diagnostic, described in patents and patent applications incorporated herein.

Selective Target Monitoring (STM)

The cell is a complex system functioning in equilibrium. The prediction of cellular function, or state, such as virus infection, neoplasia or other, is difficult because of the large number of interacting molecules and subsystems. The normal cell, as well as any pathologic cell, should be analyzed and compared on multiple levels in order to verify the pathologic cell presence in a diagnostic process.

Many levels of specimen evaluation can provide the information necessary for quality diagnostics by multi-level confirmation of the diagnostic result. These include electron microscopic/cellular and cellular structural observations, cell surface marker and nuclear surface marker production in a pathologic cell, intracellular nucleic acid such as DNA and RNA in a pathologic cell, and intracellular and extracellular protein production in a pathologic cell. Detection may also include protein analysis of the serum or plasma supernate, or the separation of the cellular cytoplasm and the nucleoplasm, which are assayed separately to present a complete picture of the disease state.

The present invention comprises methods and compositions for multilevel diagnostic assays as described herein. Multi-level disease diagnostic assays allow:

1) confirmation of a pathologic diagnosis in an assay on multiple levels;
2) assessment of the current stage of a disease during its entire time-course, and to define the current disease state and stage;
3) detection of the presence or absence of critical factors that would effect the pathologic state progression or regression (risk factors); and,
4) the development of optimal therapeutic regimens, such as determination of host susceptibility and resistance to the therapeutic agent or agents.

Target Signal Amplification in STM

STM cellular diagnostic technologies function on a cellular or nuclear membrane level to diagnose the presence of a pathologic or other cellular target, usually a cell or nuclear subset. A preferred embodiment comprises use of CMSA methods for signal amplification for the sensitive detection of the pathologic cell or nucleus. CMSA is based upon the activation and fixation of complement by addition to the target cell of an antibody specific to a cell surface or nuclear membrane protein. In eucaryotic cells, the classical complement activation pathway is activated and the extent and target presence monitored by production of the C3a peptide. In prokaryotic cells, surface carbohydrates similarly participate by activation of the alternate complement fixation pathway also resulting in the production of the C3a peptide. One embodiment of CMSA, called MACMSA, comprises use of a soluble immunogen found in the cytoplasm or released into the cellular environment. These methods and compositions are used to diagnose the presence of pathologic or other specific soluble immunogens in the cytosol or those released into the surrounding media. The diagnostic assays of the present invention are able to accurately diagnose the presence of the disease state and also determine the position of the patient in the time-course of the disease or other process.

Signal amplification in STM on a cellular or nuclear level is directly proportional to the extent of complement fixation and activation. The cell surface membrane and nuclear membrane protein markers react with the specific monoclonal or other antibody to the immunogens resulting in fixation and activation of complement. Also cell surface polysaccharides and other materials fix and activate complement via the alternative pathway. The extent of complement fixation may be monitored as a function of the number of C3a peptides produced upon activation of fixed complement molecules, known to those skilled in the art.

Membrane Assisted Complement Mediated Signal Amplification (MACMSA) and Target Signal Amplification The methods and compositions comprising MACMSA comprise embodiments that function at the molecular level by using compositions comprising attachment of an antigenic epitope or a peptide comprised of numerous epitopes to an oligonucleotide that acts as a reporter probe in nucleic acid assays. One embodiment of MACMSA comprises using a single epitope to produce increased numbers of C3a molecules after binding of antibody sensitized RBC stroma to the epitope in the presence of complement followed by complement fixation and activation.

The extent of complement fixation and activation is influenced by many factors. These factors include avidity of the epitope and monoclonal antibody, and concentration of key intermediates in the complement cascade. For example, spiking native complement with additional C3 will increase the numbers of C3a produced by the presence of a single epitope in the assay. Other factors are determined by the method of complement fixation employed, either the classical or alternate pathway and the relative effect of C3 spiking on complement fixation by each; and the use of sensitized RBC stroma used to amplify the C3a production signal from a soluble immunogen, and methods of quantification of the resulting C3a peptide. The factors influencing C3a production in MACMSA, when optimized, can provide significant C3a peptide production.

Another embodiment of the present invention comprises using a peptide with many epitopes that affords multiple Ag/Ab (antigen/antibody) reactions by use of a monoclonal antibody cocktail, with each antibody being specific to a different epitope on a single reporter probe. This results in fixation of an increased amount of complement, and generation of an increased amount of C3a peptides, yielding increased levels of signal amplification from a single target. Alternately, in another embodiment, multiple reporter probes are used to provide increased C3a production and signal amplification effect.

One embodiment of the present invention that provides enhanced complement fixation by a reporter oligonucleotide is to use an immunogenic peptide with multiple epitopes conjugated to an oligonucleotide as a reporter probe. Oligonucleotides that can be modified by attachment of proteins are known to those skilled in the art.

MACMSA is another preferred embodiment for performing signal amplification from an epitope on a reporter probe that has the ability to generate tens of thousands of signals (ICPs) per single epitope.

Signal Amplification Generated by a Single Complement Fixing Epitope on a Reporter Probe Antigen/antibody interactions are known to fix and activate the classical complement pathway and result in production of the ICPs (inactive complement peptides). The full extent of the signal amplification from a single antigenic epitope is realized if multiple IgG molecules are in close proximity at the Ag/Ab binding site, and if a lipid membrane is also available in close proximity to support the full signal amplification effect of the complement cascade, namely, enhanced C3a production. Any method may be used by those skilled in the art to provide these requirements; however, a preferred embodiment follows.

In one embodiment a biotin antigenic epitope is conjugated at any position on a reporter oligonucleotide. The addition is preferably at the time of oligonucleotide synthesis and not a post-synthesis modification. The epitope can be added to the appropriate phosphoramodite to enable synthesis; however, the epitope can be added by any other method known to those skilled in the art.

In the methods and compositions of TPA (Target Protection Assay) embodiments disclosed in the patents and patent applications incorporated herein, the reporter probe is added to a stationery or fixed protected nucleic acid sequence (PNAS) and is located on a microtiter plate wall or magnetic bead surface or any solid support. In MACMSA, the signal amplification methods for indicating the presence of the PNAS comprise a lipid membrane involvement to support the full and complete signal amplification effect. Plates or magnetic beads can be lipid coated, and antibody linked. A preferred embodiment of MACMSA uses sensitized red blood cell stroma that may be produced by any method known to those skilled in the art.

Production of Sensitized RBC Stroma

A preferred embodiment for production of RBC sensitized stroma employs the production of an IgG antibody pair, more preferably each IgG antibody has a different specificity. For example, one IgG of the pair is an IgG anti-Rh monoclonal antibody used to attach the antibody pair to the RBC surface, without any need for chemical modification of the RBC. The second IgG of the pair is an IgG anti-epitope monoclonal antibody used to bind the epitope present on the reporter probe and to fix and activate complement.

The red blood cells carrying the Rh determinants allow attachment of the antibody pair to the RBC membrane. A benefit of using the Rh determinant is that the Rh/anti-Rh complex is known to not fix complement. Any other Ag/Ab pair could also be employed in the methods and compositions of the present invention. RBCs with Ab pairs are referred to as sensitized.

The sensitized RBCs are washed and lysed in a hypotonic buffer solution and the resulting membrane material is referred to as stroma. The stroma is washed to remove RBC contents and resuspended in a suitable buffer. The stroma may now be used as a reagent.

Addition of stroma, the reporter probe with epitope and fresh complement and cofactors allows maximal C3a production. The solution may now be assayed for C3a peptide production by use of any procedure known by those skilled in the art, such as ELISA and sensitized RBC lysis or any other method.

The present invention comprises signal amplification that is generated by a complement fixing molecule on a reporter probe that comprises a polysaccharide. Polysaccharides and other materials are known to fix and activate complement by the alternate pathway and result in production of the ICPs discussed herein. The signal generated by a single polysaccharide moiety can be multiplied by tethering a complex carbohydrate chain of many molecules that fix and activate complement via the alternate pathway. This chain can be any material or polymer known to those skilled in the art that functions in these methods and can include the use of a glucan, peptidoglyan, or complex polysaccharide. In the case of a peptidoglyan linkage to a reporter probe, both the classical and alternate complement activation pathways may be simultaneously used to fix and activate complement due to the presence of polysaccharides (such as n-acetyl glucosamine and n-acetyl muramic acids) that have peptide linkages thereby activating both pathways.

The present invention comprises signal amplification that is generated by a complement fixing molecule on a reporter probe that comprises histones and other protein molecules having affinity for the reporter oligonucleotides. A region can be constructed on any reporter probe that has affinity for any molecule or molecules that after binding will fix and activate complement. Antigen/antibody complexes can be used to fix complement. Such antigens can include histones and proteins such as those used in operon regulation of nucleic acids. Molecules that do not fix C1, but instead, activate the alternate complement pathway include particulate polysaccharides, particulate lipopolysaccharides, endotoxin, trypsin-like enzymes and antigen/antibody complexes formed by IgA and IgG4 that do not fix complement. Any pair of molecules (affinity molecules) that appear on the reporter probe and its affinity pair may fix and thereby activate complement.

Some embodiments are characterized as follows:

| Reporter Conjugated Moiety | Complementary Affinity Molecule | Moiety Fixing Complement | Pathway Involved | Signal Amplification Strategy |
|---|---|---|---|---|
| Biotin | Streptavidin | Streptavidin | Classical | MACMSA |
| Unique DNA sequence | Histone | Histone | Classical | MACMSA |
| Unique DNA sequence | Repressor Protein | Repressor Protein | Classical | MACMSA |

A Novel Method for Capping the 3' End of an Oligonucleotide

The present invention also comprises use of enzymes in its methods. In some embodiments it is necessary to cap the 3' end of an oligonucleotide in a duplex structure to prevent EXO III activity (a 3' to 5' degradation double-stranded exonuclease). A novel capping method produces an overlap on the 3' end of an oligonucleotide that pairs with no other associating probe and results in an overhang preventing blunt end nuclease activities.

This is achieved by production of the oligonucleotides by an enzymatic as opposed to a chemical synthesis. Use of Taq Polymerase and PCR technology to produce the oligonucleotide to be capped on the 3' end results in additional terminal synthesis of an extra adenine (A) residue at the 3' end as well as the presence of the polymerase protein. The presence of either or both of these will protect the target probe complex or PNAS from EXO III activity, which requires the presence of a blunt end and not an end possessing an overhang, or a, protein, enzyme molecule.

Characterization of STM

In a preferred embodiment, the STM process selectively binds antibody to a target cell or membrane antigen not found on the other cells present, and then activates the complement system by fixation in the presence of all the complement components. It is known to those skilled in the art that an antigen/antibody complex comprising one IgM molecule or 2 IgG neighboring molecules will fix complement. Therefore a target cell or membrane with thousands of identical pathologic surface markers interacts with multiple antibody molecules and is capable of fixing and activating numerous complement molecules. The end result of complement fixation and the reaction of the complement cascade is generally the breaking open of the target cell or nucleus, while cells that do not possess the target antigens remain untouched. Though the discussion herein uses neoplastic detection as an example, the present invention contemplates the detection of any target, including but not limited to neoplastic changes, infectious targets or carcinogens.

This selective lysis of the target, for example, a cell or nucleus, and lack of effect on other tissue cells, insures that the contents of the other normal cells do not interfere with detection of the markers and contents of the target cell. An example of an embodiment of the present invention comprises isolating the nucleus of the whole cell using early protein markers present in the early pathologic state as the target antigen. The present invention identifies low copy number targets in a large mass of normal sample material by negating the non-target contribution from the contents of normal tissue.

The STM methods allow the pathologic target cell or nucleus to be isolated from normal cells/nuclei, and present a multiphasic (molecular and supramolecular) approach to examining the cell population. For example in a dysplasia assay, the assay separates and detects the earliest dysplasia markers by detection of the target pathologic cell at three levels. One level is the detection of isolated nuclei where the earliest dysplasia can be found in a low grade squamous intraepithelial lesion (LSIL). A second level is the detection of isolated cell membrane ghosts of the specific pathologic cells with dysplastic markers of another type called high squamous intraepithelial lesions (HSIL) representing late dysplastic states and early and late neoplasia; and a third level is the cytoplasm of the entire cellular sample where Haystack Processing technologies will be used to confirm detection by direct mRNA analysis. For example, the RP-TFO (Reverse Phase-Triplex Forming Oligonucleotide) format analysis provides direct mRNA analysis specific for these markers, that confirms the diagnostic result.

An embodiment of the present invention comprises methods for the analysis of pathologic nuclei and cell membrane ghosts. Surface protein markers are detected by their reaction with specific IgG or other monoclonal antibodies. Though monoclonal antibodies are used herein, it is contemplated by the present invention that any type of antibody or antibody fragment that is capable of functioning with complement proteins to fix and activate them can be used in the methods and compositions of the present invention. If the earliest detection site, such as the cell nuclei, indicates the initiation of dysplasia, subsequent or simultaneous detection should be corroborated in the secondary cell surface site. This interaction of two dysplastic/neoplastic marker panels will support the earliest detection of dysplasia.

The next diagnostic site to be tested by the methods of the present invention is the cytoplasm of the entire cell cytoplasm searching for the mRNA specific for the markers previously presented in the two dysplasia/neoplasia panels. This test confirms the presence of a pathologic state at the molecular level, and also rules out any contribution of some non-specific effect on the diagnostic process. This conformational step adds to the specificity of the STM methods. In one embodiment of the present invention, (see FIGS. 5A, 5B and 6) nuclei and cytoplasm are simultaneously isolated and configured in such a manner that the independent analysis of particulate membranes, both cellular and nuclear, for marker proteins and nucleic acids provide multiple confirmations of a pathologic state.

In the assays of the present invention, upon antibody reaction with the pathologic dysplasia marker in the presence of the complement proteins, surface antigen/antibody complexes fix and activate complement molecules, as well as support the compartmental release of target nuclei, cytoplasmic protein and nuclear protein, and nucleic acid. The signal generated by the reactions of the complement fixation and activation support high sensitivity and specificity in target detection. Furthermore, the signal can be amplified to detect the presence of low cell or nuclei numbers which are present at an early stage in the disease time-course.

The present invention comprises methods and compositions to amplify signals for target detection. Target detection is based on the presence of numerous and varied surface markers on the target, preferably in a membrane, which are not present on normal cells or membranes. Each antigen/antibody complex can fix at least one molecule of complement and one can realize at least a thousand-fold increase in signal by detecting the complement molecules fixed by the total cellular or nuclear antibody complexes. For example, a single target cell or nucleus can fix and activate at least $10^3$ complement molecules.

In these embodiments of STM, complement fixation and activation is quantified by a novel method, namely detection of production of the inactive complement peptides (ICP), C3a. Detection of the ICPs, preferably C3a, is achieved by assays for proteins or peptides that are known to those skilled in the art, including but not limited to, competitive and sandwich immunoassays such as ELISA assays, immunoMTRF or assays included in the present invention such as complement mediated signal amplification (CMSA) and lysis of sensitized RBCs, and lysis of liposomes containing fluorescence and quencher molecules.

Complement is a group of at least 25 glycoproteins with varying electrophoretic mobilities. Most circulate in the blood in an inactive precursor form and have effects in the body only after activation. Two major functions of complement in vivo are to promote the inflammatory response and to alter biological membranes to cause direct cell lysis or enhanced susceptibility to phagocytosis. Cell lysis occurs when antibody-mediated complement is fixed and activated by sequential interaction of the entire complement cascade. Most of these interactions result in the cleavage of an inactive protein with the release of small peptides in the complement response. In vitro these peptides have no function, or are called inactive complement peptides (ICPs). The peptides that do not participate in a direct complement response, meaning the lysis of cells or the opsonization of cells, are referred to herein as inactive complement peptides (ICPs). These inactive complement peptides (ICPs) have multiple in vivo functions: chemotaxis, enhancement of phagocytosis, alteration of vascular permeability, and stability of cell membranes (platelets and granulocytes). In a few instances, inactive proteins aggregate resulting in an active protein.

The Classical Complement Pathway Cascade:

The first complement component C1, attaches to the Fc portion of immunoglobulin molecules that have the appropriate binding site in the CH2 domain of the heavy chain. All mu ($\mu$) chains have this site, and most gamma ($\gamma$) chains. C1 is composed of 3 subunits: C1q, C1r, and C1s held together by calcium ions. If IgG is the type of antibody used, two adjacent protein antigenic sites must each bind an antibody molecule to form a doublet arrangement to provide the specific conformation for binding of the C1 complex. One IgM pentamer can bind the C1 complex. C1q binding to the FC region of the antigen/antibody complex undergoes a conformational change that activates C1r, which in turn activates C1s, and fixes complement.

The following represent the steps in complement fixation and activation resulting in the production of the ICPs (C2a, C4a, C3a, and C5a).

Each molecule of C1q bound or fixed to the target membrane will produce at least an equivalent number of C3 convertase molecules and the ICPs, C2a, C4a, C3a, and C5a. At least one C3 convertase molecule is formed per one C1q molecule initially bound. Thousands of surface membrane proteins are expressed on a single cell, thus activation of complement fixed by multiple sites on a single cell or nuclear membrane can produce thousands of C2a, C4a, C3a, and C5a ICPs.

C1s propagates the complement sequence by cleaving C4 into C4a and C4b and cleaving C2 to uncover a labile binding site. C4b contains a binding site and attaches to the cell membrane. C4a is released into the solution in vivo to stimulate anaphylaxis by stimulating mast cell degranulation and histamine release, thereby increasing vascular permeability. This released peptide may be used in the present invention to amplify the signal from a target.

C2 attaches to the C4b molecule on the cell membrane. The larger fragment C2b combines with C4b to produce C4b2b, called C3 convertase, which possesses enzymatic activity. Each initial C4b2b molecule (C3 convertase) can generate attachment of hundreds of additional C4b2b (C3 convertase) active complexes to the cell membrane in proximity to the C1q binding site (the lipid structure is a requirement for this event), and in doing so, releases additional C4a and C2a ICPs which can be used for signal amplification methods in the present invention.

The third step, also an amplification reaction, is based on the function of all the bound C3 convertase molecules (C4b2b) to each cleave hundreds of C3 molecules in solution resulting in release of additional C3a peptide fragments into the solution. This peptide has anaphylatoxin activity in vivo, and will be exploited as a signal amplification marker method in vitro. The C3b larger fragment binds to the cell membrane complex or decays in solution. C3b fragments by themselves are not active catalytically and do not promote cell lysis but do increase phagocytosis upon attachment to the cell (opsonin activity in vivo). The importance here is the additional production and release of C3a into the solution in vitro and plasma in vivo.

Some C3b molecules join the extensive numbers of C3 convertase attached to the entire cell membrane forming C4b2b3b5b or C5 convertase releasing the C5a ICP into the solution.

In the presence of C5b, molecules of C6, C7, and C8 and a variable number of C9 molecules, assemble themselves into aggregates in the presence of $Zn^{+2}$ called the membrane attack complex (MAC). The complex compromises the integrity of the cell membrane by altering permeability of the membrane and results in cell lysis.

The Alternate Pathway Complement Cascade

Cleavage of C3 and subsequent activation of the remainder of the complement cascade occurs independently of complement fixing antibodies. Cell surface particulate polysaccharide and lipopolysaccharide molecules, endotoxin, trypsin-like enzymes, and Ag/Ab complexes of IgA, and IgG4, that do not activate C1, all function to activate the alternate pathway. The activation is mediated by the cleavage of C3 into C3a which is released in solution and C3b. This molecule would be rapidly degraded in the fluid phase (classical pathway), but in the alternate pathway, C3b becomes stabilized by binding to the surface of a particulate activator of the alternate pathway called factor B, forming a stable C3b-factor B complex, itself interacting with a serum protease (factor D), cleaving factor B to produce C3bBb, that functions as a C3 convertase, again catalytically producing many additional C3a peptides.

The alternate complement activation pathway is activated by all viruses, bacteria, yeast or any other microbe containing polysaccharide or lipopolysaccharide elements in its exterior cell wall.

One embodiment of the present invention, the novel in vitro use of the complement cascade and the generation of the ICPs in the amplification of a signal to detect very low copy number of targets, is described herein.

Signal Amplification in STM

The present invention comprises novel and sensitive methods for signal amplification, called CMSA and MAC-MSA. Activation of the complement cascade results in the production of millions of inactive complement peptides (ICPs). Analysis of the sample for the detection and quantification of the ICPs results in the generation of 40 million ICPs per pathologic cell membrane, or nucleus, and generation of 40,000 ICPs per nucleic acid target (epitope) with the involvement of complement fixing Ag/Ab reactions in proximity to a lipid matrix (MACMSA).

Table I summaries the production of the ICPs and theoretical quantification provided by CMSA.

TABLE I

ICPCharacterization and Quantification in CMSA

| $10^3$ sites to fix C' per membrane surface (First Amplification Step) | Nature of ICP generated | Number ICPs produced based on binding of each C1s module |
| --- | --- | --- |
| C1q, C1r, C1s | NONE | NONE |
| C4b | C4a | $10^3$/cell or nuclear membrane |
| C4b2b3b | C3a | $10^3$/cell or nuclear membrane |
| C4b2b3b5b | C5a | $10^3$/cell or nuclear membrane |
| C6,7,8,9 | NONE | NONE |
| (Second Amplification Step) | | 200 fold increase in ICPs |
| C1q, C1r, C1s | NONE | NONE |
| C4b | C4a | $200 \times 10^3$ $2 \times 10^5$ per C1s bound |
| C4b2b3b | C3a | $2 \times 10^5$ |
| C4b2b3b5b | C5a | $2 \times 10^5$ |
| C6,7,8,9 | NONE | NONE |
| (Third Amplification Step) | | 200 fold increase in ICPs |
| C1q, C1r, C1s | NONE | NONE |
| C4b | NONE | NONE |
| C4b2b3b | C3a | $200 \times 2 \times 10^5$ or $4 \times 10^7$ or 40 Million (theoretical) |
| C4b2b3b5b | C5a | Not amplified here (same value as amplification step number 2) NONE |
| C6,7,8,9 | NONE | NONE |

SUMMARY: ICP numbers produced in CMSA based on the presence of a single pathologic target cell
• Primary Amplification Step
$3 \times 10^3$ ICPs
• Secondary Amplification Step
$6 \times 10^5$ ICPs
• Tertiary Amplification Step
$4 \times 10^7$ ICPs
Total ICPs generated per single pathologic target
$4.0603 \times 10^7$ ICPs 40 Million This estimation is made by reducing the ICP generation 1000-fold, due to the ability of a single immunogenic epitope to fix 1000-fold less complement than an average cell membrane.

A preferred ICP is the peptide fragment C3a, because it is found in very high numbers after complement fixation. Production of other ICPs (C4a, C2a, and C5a) may also be detected although they provide less than one percent of the total signal generated by the detection of a single pathologic cell, nucleus, or nucleic acid species.

In general, the novel in vitro use of the complement cascade to quantify the presence of a pathologic cell or nucleus is based upon monitoring the extent of complement fixation and activation as a function of the number of inactive complement peptides (ICPs) that are produced. Basically, each target cell fixes thousand of complement molecules after addition of antibodies specific for the target cell surface protein and the subsequent reaction with the complement cascade. The initial complement molecules that are fixed can themselves exert an additional 200-fold amplification effect. These complement molecules also provide for another 200-fold signal amplification effect later in the course of the complement cascade. This results in the following theoretical total signal amplification profile in CMSA a) Multiple cell surface protein markers on the dysplastic cell each fixing complement, yielding 1000-fold amplification per pathologic target, b) Primary 200-fold amplification during early stages of complement fixation, c) Secondary 200-fold amplification at a later step in the complement cascade. Total 40 million ICPs produced per target.

In MACMSA, the following represents the total signal amplification profile:

a) A single soluble protein or reporter immunogenic epitope fixes one complement molecule.

b) Primary 200-fold amplification effect during early stages of complement fixation that is lipid membrane dependent requiring the use of the RBC sensitized stroma reagent.

c) Secondary 200-fold amplification at a later step in the complement cascade (membrane independent). Total 40,000 ICPs produced per target.

The signal generated by CMSA can approach 40 million ICP produced per single pathologic target and the interactive presence of a lipid matrix, for example the cell or nuclear membrane.

An example of the methods of the present invention comprises steps of the complement cascade and detection of ICPs. Sequential cleavage of many complement components generates small peptides (ICPs) released to the solution, and a large active protein that attaches to a target surface where the antigen/antibody complex is bound, initiating additional complement activation. After a cascade of complement proteins interacts with the antigen/antibody/complement complex on the membrane surface, generally, the cell or nuclear membrane may be perforated by late complement cascade proteins (MAC complex).

In one embodiment of the present invention, the cell membrane or nuclear membrane is used to produce the ICPs, but an inhibitor of the membrane attack complex is added to prevent lysis of the membranous sack and its contents. This results in washed intact cells and nuclei and avoids background signal interference from the potential release of normal cell cytoplasm or nucleoplasm of the cell or nucleus and other normal cell components as well.

The cells or nuclei being tested can be washed to remove extraneous proteins once they undergo partial complement reaction without lysis, referred to herein, as withheld lysis. Withheld lysis can be achieved by chelation of $Zn^{+2}$, a requirement for lysis by EGTA addition or any method known to those skilled in the art. Once the cells or nuclei are isolated, they can be treated by a post-wash to overcome the inhibition of the membrane attack complex (MAC) proteins (C6, C7, C8, C9) and addition of excess $Zn^{+2}$ and fresh complement will now selectively lyse this pathologic cell or nucleus and facilitate collection of the unique membranous cellular and nuclear contents in different compartments. The cations of calcium and magnesium are required to hold associating protein complexes together that are activated by the fixation of the C1 molecule to the antigen/antibody membrane surface complex, while $Zn^{+2}$ cations are required for the activity of the membrane attack complex.

The cytoplasm and nucleoplasm of the target cells once released by overcoming lysis inhibition, can provide DNA, mRNA, and protein fractions which can be analyzed by detection systems including the Haystack Processing technologies, exemplified by DNA TPA, RP-TFO, mRNA RP-TFO, and immunoMTRF as well as the MACMSA technique and assays described in related documents. For surface membrane proteins that are transcriptionally controlled, the presence of the surface membrane protein can be verified by mRNA and protein analysis of the cytoplasm protein and nucleoplasmic mRNA analysis, using MACMSA, without non-specific signal generated by normal cell contents, supporting a lower background signal in assay negative controls.

Signal Amplification

Methods of signal amplification using the classical complement pathway employ methods of CMSCA and MACMSA. Signal amplification methods for the alternate pathway is similarly initiated by a step wherein a thioester on native C3 binds to polysaccharide, such as a polysaccharide on the surface of an organism. Next, the complex is stabilized by the binding of Factor B and its subsequent activation:

C3bBb=activated Factor B or C3 convertase

The first signal amplification step occurs by the convertase cleaving numerous native C3 molecules producing numerous C3a peptides and additional C3b molecules that attach to the complex to form additional C3 convertase, that release additional C3a in the solution.

The C3 convertase (C3bBb) cleaves hundreds of C3 molecules generating additional C3b molecules, which attach to the complex and amplifies its activity. Cleavage of the C3 mediates release of hundreds of C3a ICP molecules to mediate amplification in vivo of the immune response and in vitro signal amplification.

The second level of signal amplification employs the aggregation on the surface of a microorganism or a protein aggregate of numerous C3b units, Factor B, and Properdin (stabilizing protein) acts as a potent C5 convertase producing hundreds of C5a (ICPs), thus cleaving C5 to an active C5b and release of a C5a into the solution. The remainder of the complement cascade is identical to later steps in the classical pathway. Thus, the ICPs, generated by complement fixation of the classical complement pathway, or the alternate complement pathway are used for in vitro signal amplification target detection strategies.

Stochiometry of ICP Production Via the Classical Complement Pathway (See Table I)

In Table I, it is represented that three levels of C3a production or signal amplification occurs based upon CMSA treatment of a cell or nuclear membrane.

First, thousands of surface protein molecules on a single cell or a single nuclear membrane fix thousands of C1 molecules producing a minimum of thousands of C3a peptides post complement fixation.

Second, there exists a 200-fold amplification per each of the C1a molecules fixed due to the presence of the membrane proximity component for complement activation.

Third, there exists an additional 200-fold amplification per each of the $2\times10^5$ bound C3 convertase (C4b2b3b) molecules by cleavage of additional solution C3 and formation of additional C3a peptide for a total of $4\times10^7$ or 40 million molecules of C3a peptide generated per target membrane.

Theoretical Stochiometry of ICP Production Via the Alternate Complement Pathway

C3a production by the alternate pathway must be empirically determined. Similar signal amplification quantification can be configured based on the cyclic C3 convertase enzymatic complexes formed. Though not wishing to be bound by any particular theory, it is believed that the absolute numbers of ICPs produced in the alternate pathway are on the same order of magnitude or greater than that observed by complement fixation and activation via the classical pathway.

Detection and Quantification Assays for the ICPS (C4a, C2a, C3a, C5a)

Many assay strategies are available to determine the presence and quantification of the individual or combined ICPs. The present invention comprises assays for measuring the presence and number of individual or combined ICPs and is not limited to the assays and embodiments disclosed herein. The individual ICPs can be quantified by assays for proteins, including but not limited to sandwich ELISA assays, or similar assays that use a capture antibody bound to a solid support and a different labeled reporter antibody both specific for different epitopes on each ICP (C4a, C2a, C3a, C5a).

For example, an embodiment of the C3a sandwich ELISA assay is configured using a biotinylated anti-C3a reporter antibody and is followed by addition of an IgG anti-biotin alkaline phosphatase polymer conjugate to facilitate signal generation per C3a molecule by introduction of the substrate, 1,2-dioxetanes. Any other enzyme known to those skilled in the art may be used to quantify the number of C3a molecules. The enzyme may provide a color signal, a fluorescent signal, or a chemiluminescent signal, all known to those skilled in the art.

A preferred embodiment of the signal generated by the C3a peptide molecules is mediated by the use of an anti-biotin alkaline phosphatase polymer, known to generate 4 logs of signal per polymer molecule. The polymer is then reacted with a chemiluminescent substrate generating a stable light signal. One such substrate is the 1,2-Dioxetanes, which have been shown to detect 0.01 attomole quantities of alkaline phosphatase enzyme, translating to a ten-fold increased level of target detection by the enzyme polymer. This detection system will support unprecedented high levels of target detection and, due to the nature of antibody conjugates to enzymes, will provide a relatively low background in the negative controls.

Such methods may also be automated. An example is shown below.

Step I. Prepare a magnetic bead with a covalently bound IgG anti-C3a capture antibody. The binding can be achieved by any chemistry known to those skilled in the art such as covalently linking a carboxylated magnetic bead to the primary amine on the n-terminal end of the antibody molecule, or any other chemistry known to those skilled in the art.

Step II. The magnetic bead is washed to remove non-bound capture probes and

Step III. Conjugated beads are added to a sample containing the C3a peptide in solution, which is mixed and incubated.

Step IV. The magnetic beads are washed to remove non-specific bound materials

Step V. Add another antibody, IgG anti-C3a, which has reporter function and is specific for a different epitope on the C3a peptide molecule. This antibody possesses an alkaline phosphatase (AP) polymer covalently attached to it. This may be generated by any method known to those skilled in the art, the preferred one being attachment antibody N-terminal amine of the maleimide derivative of the AP polymer, which results in covalent bond formation. Any other chemistry may also be employed.

Step VI. Wash to remove unbound reporter probe. The number of washes and the wash buffer may be critical in resolving non-specific signal from unbound reporter enzyme.

Step VII. Add the magnetic beads to a solution containing the 1,2-Dioxetane substrate and incubate under conditions for the production of a stable chemiluminescent signal.

The reporter antibody, and hence the target, is detected by the activation of a chemiluminescent substrate to produce light by enzymatic catalysis.

The reporter antibody can also be detected using immunoMTRF methods as disclosed in U.S. patent application Ser. No. 09/443,633 or by conjugating a label, such as a single molecule of fluoroscein isothiocyanate, to each ICP reporter antibody.

Another method of the present invention for C3a quantification comprises steps to identify and quantify the specific ICP of interest using sensitized RBCs conjugated with anti-specific ICP antibodies, that will only react with the free-floating ICPs in solution. In this embodiment RBCs linked to anti-ICP monoclonal antibodies will in the presence of complement undergo complement-mediated immunoerythrocyte lysis, releasing hemoglobin for quantitation.

The extent of RBC lysis is directly proportional to the quantity of ICPs produced and targets present.

Another method for assay of C3a production would be the use of IgG anti-C3a antibody imbedded on the surface of a liposome containing fluorescence and quencher molecules in close proximity, so that no fluorescent signal can be detected. Introduction of a C3a peptide to the antibody sensitized liposome, in the presence of the complement components will result in complement mediated lysis of the liposome, releasing the fluorescence and quencher molecules into the solution. Their release and separation can be monitored by the detection of a fluorescent signal. The extent of liposome lysis is directly proportional to the quantity of ICPs produced and targets present.

Generation of Sensitized RBCs for C3a Assay: RBC Enzyme Treatments

One embodiment of the present invention comprises methods to identify and quantify specific ICPs of interest comprising use of sensitized RBCs that are conjugated with specific anti-ICP antibodies that will only react with the free-floating ICPs in solution and in the presence of fresh complement, result in red blood cell lysis upon binding of free ICPs with subsequent complement fixation and red blood cell lysis.

The sensitized or immunoRBCs can be generated by stripping the RBCs with a proteolytic enzyme such as bromelain, ficin, or papain and by other methods known to those skilled in the art, that attach the ICP specific antibodies to the RBC surface, producing sensitized immunoerythrocytes which bind the free floating ICP in solution. This attachment of an antibody to the stripped RBC surface by simple exposure of the antibody to the erythrocyte provides a non-covalent attachment of the antibody molecule, and is sufficient for some applications. Due to the fact that chemical modification of the RBC surface involves increased fragility of the modified RBC, which may result in the spontaneous release of hemoglobin and make quantification of the ICP peptides difficult, other methods are also contemplated by the present invention.

A novel process for production of antibody sensitized RBCs is mediated by the use of an IgG antibody pair. The characterization of the molecule is as follows:

1. Two IgG molecules are attached to each other by any method known to those skilled in the art, where the attachment does not interfere with the antibody binding sites.
2. One antibody must be specific to any of the ICP peptides for assay; for example, the IgG anti-C3a antibody used in the C3a peptide assay. Other embodiments require this antibody to be specific for any immunogenic epitope on the target.
3. The other antibody is specific for an antigen on the RBC. A most preferred embodiment comprises use of an antibody specific for the Rh determinant. The Rh determinant extensively covers the RBC membrane with thousands of molecules and this is the site at which the antibody pair binds to the erythrocyte. This antigen/antibody reaction does not fix complement. This is important in light of the use of this immunoerythrocyte in the presence of fresh complement to monitor attachment of the C3a peptide to the complement fixing anti-C3a antibody in close proximity to the RBC surface. Any interactive antigen/antibody interaction that does not fix complement may also be employed.
4. The Rh determinants on the RBC surface are responsible for bringing the antibody to the C3a and other peptides in close proximity to the lipid membrane surface without altering the stability of the immunoerythrocyte.

The sensitized immunoerythrocyte in the presence of the corresponding peptide and fresh complement will undergo lysis by the membrane attach complex and hemoglobin will be released.

The Antibody Pair Method for in Vivo Neutralization of a Pathologic Analyte by Sensitized RBCs Another embodiment for use of the antibody-pair molecule may involve its use in vivo to neutralize the activity of a pathologic analyte. This analyte may be a viral particle, antibody molecule, dysplastic or cancer cell, and even an immunogenic environmental carcinogen. Attachment of the IgG anti Rh-IgG anti pathologic analyte antibody pair to the RBC surface would facilitate the immediate attachment and neutralization of the pathologic analyte to any of the RBCs that have been sensitized.

Neutralization of the activity of the pathologic analyte would immediately block its reactive effect and would initiate its removal from the body mediated by macrophage phagocytosis or the function of another clearance system in the spleen and liver. It is known to those skilled in the art that RBCs possessing immune complexes on their surface are rapidly cleared by these body systems.

Production of Sensitized RBC Stroma for Use in MACMSA

MACMSA requires the interaction of a lipid/antibody complex with a soluble protein or reporter probe immunogenic epitope. The preferred embodiment for production of this complex is the sensitization of the RBCs by the aforementioned method with subsequent lysis of the sensitized RBCs in a hypotonic buffer solution resulting in the production of antibody attached lipid membrane (RBC stroma) that will exert the full signal amplification effect of the immunogenic epitope or soluble protein by the MACMSA process. Stroma production is achieved by placement of the immunoerythrocytes in a hypotonic buffer resulting in RBC lysis and membrane ghost formation. The stroma is then washed in buffer and resuspended in buffer for use as a reagent.

Dysplasia/Cancer Screen

The present invention comprises multi-faceted methods for detection of disease states and these embodiments will support staging of the disease time-course important for selection of treatment modalities. The present example is directed to cervical dysplasia, but this example is only for illustrative purposes and the methods and compositions described herein can be used for detection of any cellular target, pathologic or other.

The earliest markers of dysplasia are thought to appear in the nucleus and the earliest available site for detection of the dysplastic marker is the dysplastic cell nuclear membrane. The present invention allows for analysis of only the dysplastic nuclei by separation of the target nuclei from the normal nuclei in the sample. Numerous dysplastic nuclear markers are currently available, such as those listed in Table II, and these can be screened for in a multiplex panel. Those markers may be selected whose increased presence follows the progressive timecourse of cervical metastatic development. Preferred dysplasia markers include but are not limited to, Ki-67 (MIB-1); Cdc, McM antigens: NMP(CvC-3); HMGI (Y); PCNA; and Topoisomerase II Alpha markers. Monoclonal antibodies to theses markers can be used in this part of the screen. Such embodiments of the present invention, termed the dysplasia/cancer screen can be used to address all tumors including those that possess a proneoplastic dysplastic state. Any changes in cellular condition that are first seen in the nuclei can be diagnosed using the methods and compositions of the present invention.

The earliest late dysplasia and neoplastic cell surface markers appear on the cell surface. The present invention allows one to analyze only the cell membrane alone by separation from the normal cell membrane ghosts. The cell surface membrane is the second earliest available site for detection of dysplasia or neoplasia markers. Numerous late dysplasia markers are currently available and can be screened for in a multiplex panel. Examples of these markers are listed in Table III and referred to as Multiplex Panel B. These multiplex panel markers are generally different from the early dysplasia nuclear membrane markers. Those markers may be selected whose increased presence follows the progressive timecourse of cervical metastasis. Preferred candidates are include but are not limited to, ESA; Keratin-14; and HPV-IF markers.

The present invention can be used to diagnose all tumor types and can be used to detect tumor metastasis, early tumor detection in lymph nodes and fine needle aspirates, and monitoring of residual disease in biopsies in cancer therapy. The cytoplasm of the cells can be screened for the presence of the dysplastic markers presented in Table IV: Multiplex Panel C. Those markers may be selected whose increased presence follows the progressive time-course of cervical metastasis. Preferred candidates include but are not limited to Bcl–2, GST Pi, and TdR Pase.

Once the target nuclei are unblocked for lysis, fresh complement is added to lyse them and the nucleoplasm is collected. Using the methods that have been directed to nucleic acid analysis, the present invention comprises direct mRNA analysis technology, such as mRNA TPA using the RP-TFO, to sensitively detect and quantify the presence of mRNA specific for the markers in both multiplex panel A and multiplex panel B. This molecular confirmation of the presence of marker mRNA in pre-neoplasia or neoplasia will further confirm and substantiate the diagnosis of the pre-neoplastic or neoplastic state. Furthermore, other mRNA or DNA targets for risk factors for dysplasia and neoplasia are important for screen result analysis and can be separated into an mRNA multiplex panel and a DNA multiplex panel as presented in Table V, Panel D. These risk factors include infectious agents or indicators of inflammation, such as HPV infection, presence of abnormal numbers of inflammatory cells such as polymorphonuclear leukocytes (POLYS), in the specimen, *Chlamydia trichomatis* infection and *Candida albicans* infection and others. These risk factors can be assessed as an adjunct to the multiplex panels. Another important factor in cervical screening is the presence of large infiltrations of polymorphonuclear leukocytes (POLYS) that signals the onset of a pathologic reactive process. Any species specific DNA marker can be utilized to quantitate the presence of the POLYS.

The present invention comprises both DNA assays and direct RNA detection diagnostic technologies. The advantages of mRNA analysis include detection of derepression or gene transcription that results in production of thousands of specific mRNA targets per single gene present.

Another embodiment of the present invention employs testing of the HLA typing of the individual. This assay need only be performed one time in a patients life and the results catalogued and made available for review at the time of interpretation of the test results. This assay can be performed by current serologic methods, or any other method known by those skilled in the art. The benefit of HLA typing of the individual is based on the presence of high risk factors for cervical and other cancers in the individual, that are regulated by the presence of specific HLA antigens. These HLA factors can be used to customize the screening regimen to offset the enhanced risk of dysplasia/neoplasia.

Cells making up the sample are obtained by methods known in the art. No restriction on the number of cells in the sample is necessary. Dysplastic or pre-cancerous cells are the precursors to invasive carcinomas. Ten percent of dysplastic cells, if left undiagnosed or untreated, will result in metastatic cancer. Diagnostic technology designed to detect early dysplasia needs to focus on the differences in dysplastic and normal uterine surface squamous epithelium. Normal exfoliated surface epithelial cells are well differentiated, namely, they are not actively dividing, they are programmed for cell death, and will not initiate replication of DNA. Dysplastic exfoliative surface cells lose the differentiated quiescence and actively divide without regulation. This immortalization of the cell in the superficial uterine layers results in a cessation of apoptosis (cell death) of normal cells, and the onset of abnormal proliferation of the precancerous cell.

Dysplastic cells have been studied and many unique and important markers are at hand to differentiate the dysplastic cell from a normal cell in the surface exfoliative cell layers. These markers have been identified by immunohistochemical staining of tissues and more recently by immunocytochemical staining of cells. The exfoliative cell population is known to contain not only the preneoplastic cervical cancer cell but also preneoplastic cells from closely related sites, such as the ovary. Determination of neoplastic states using only immunohistochemical methods are not adequate for diagnosis of pathological states.

The value of a dysplastic diagnostic must rely upon the detection of the minute changes from normalcy of dysplastic cells. The areas of interest focus on the initiation of chromosome replication and the loss of programmed cell death or immortality of dysplastic surface exfoliative cells. The early dysplasia markers can be found initially in the dysplastic nuclei, both in the nuclear membrane and in the nucleoplasm. These markers have their origin in the initial steps of cell cycle initiation, and chromosome replication. The immortalization of the dysplastic cell can also be considered an early step in tumorigenesis and a late step in pre-cancerous dysplasia.

The dysplasia and neoplastic markers of value in the screening of exfoliative cells are presented in Tables II, III, and IV. Table II presents those earliest markers that represent dedifferentiation of a normal cell, namely nuclear replication in a cell (exfoliative and differentiated). The first site for detection of these markers occurs on the nuclear membrane surface, as well as in the nucleoplasm. Normal exfoliative tissues are negative for these markers, while basal layer cells present these markers prior to cellular differentiation and their loss in the differentiated (quiescent) cell.

Table III presents the next earliest markers in the pre-cancerous cell. Their location is on the cellular membrane and usually bridge the gap between late dysplasia (HSIL) and metastatic carcinoma. Tables II and III illustrate that these two differing marker panels express themselves in direct relation to the stage of disease. Any inconsistencies in these tables may reflect problems in tissue staining technique or other non-specific factors. The dysplastic cell assay uses internal confirmation to distinguish very early dysplasia from any non-specific background that may be generated. Additionally, cancerous conditions, such as the presence of ovarian changes leading to ovarian cancer can not be detected easily using presently available assays, but are detectable using the methods and compositions of the present invention.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

The Dysplasia/Cancer Screen

Figure 5A:
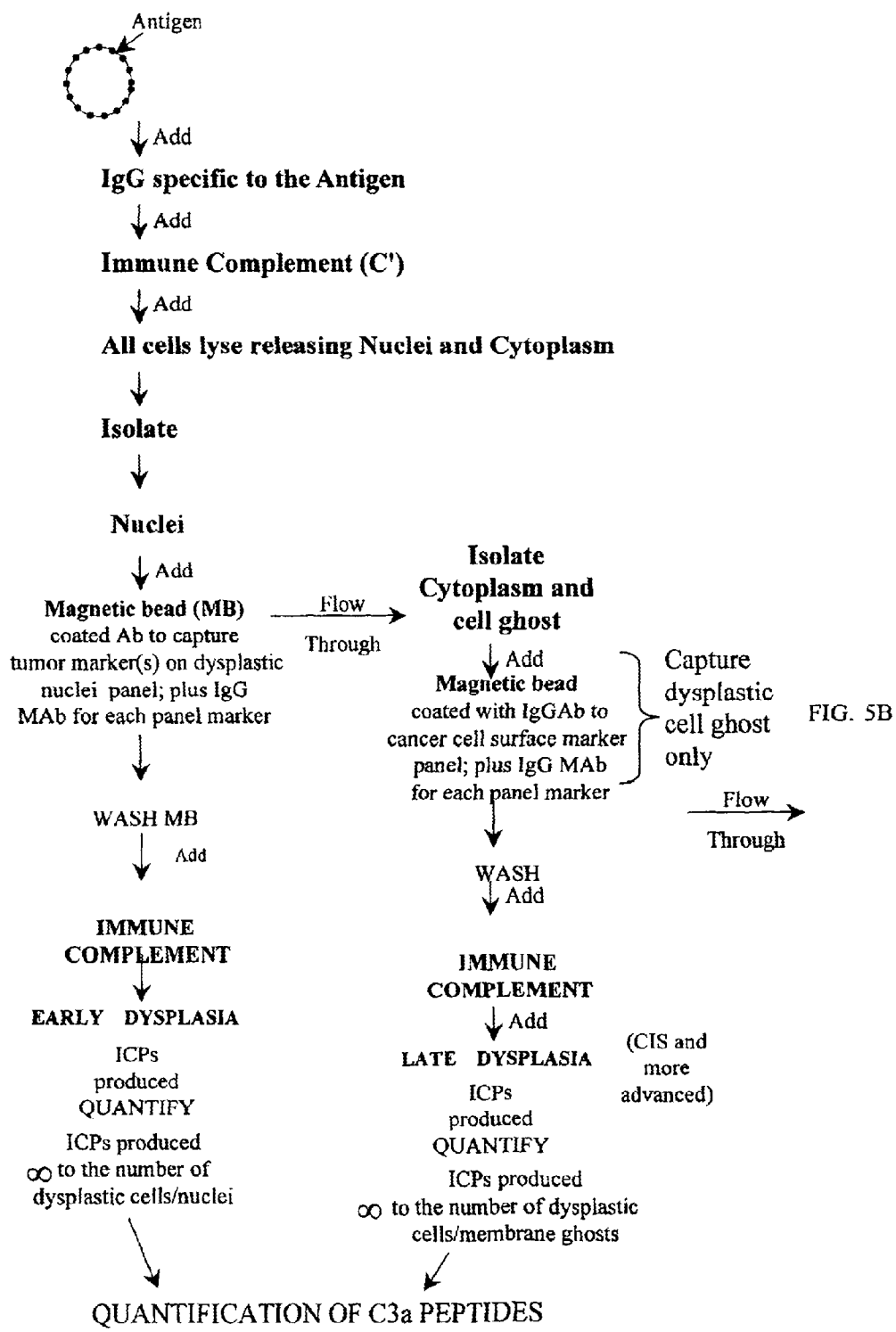
Figure 5B:
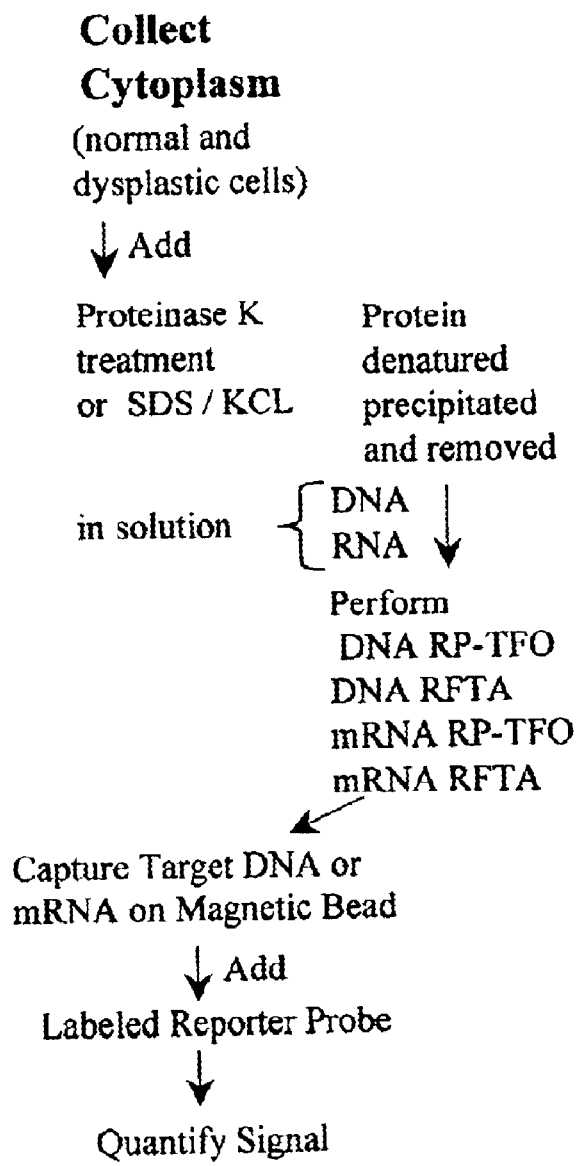
Figure 6:
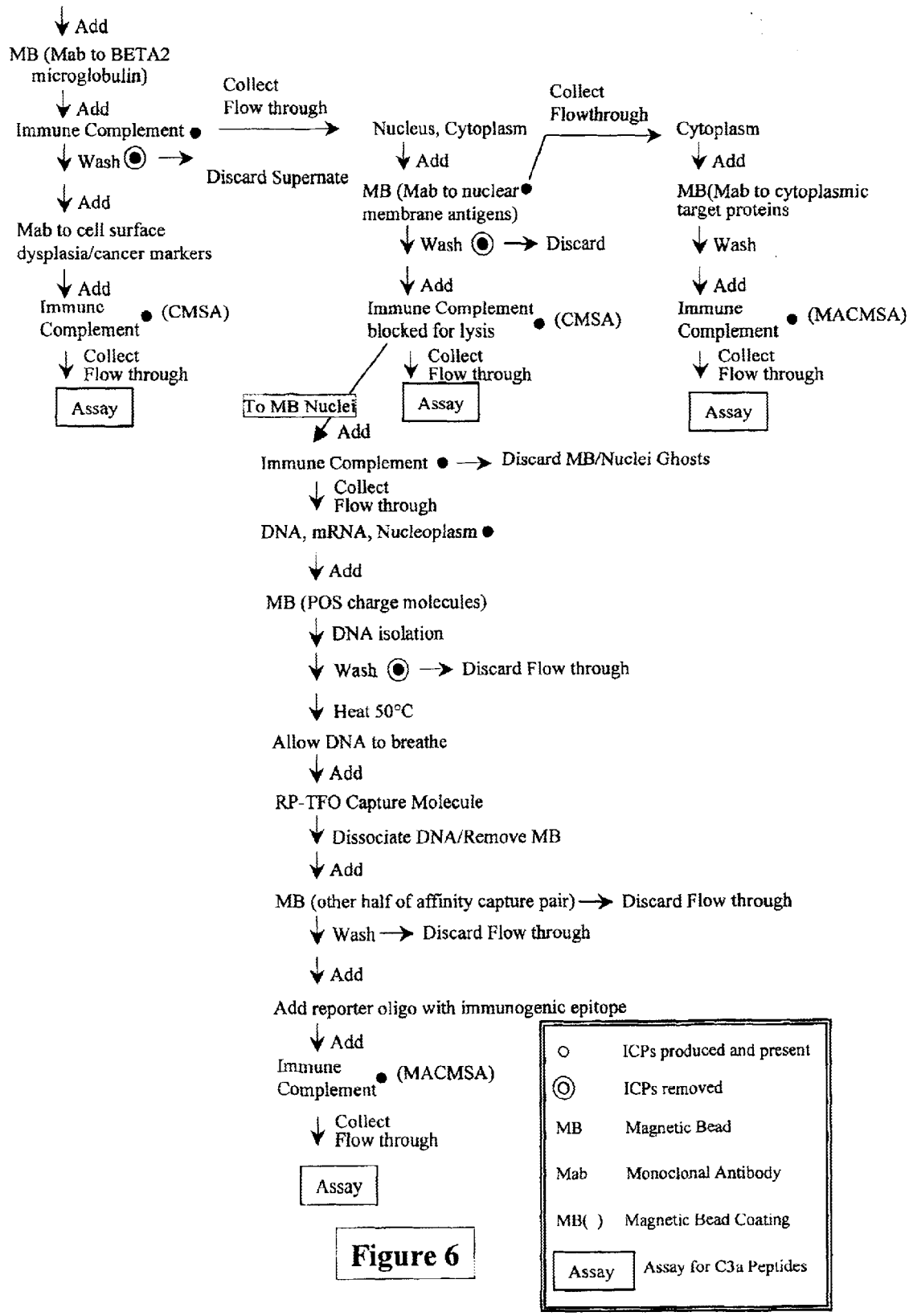

Two embodiments of the Cervical Dysplasia/Cancer Screen are presented in FIGS. 5A, 5B and 6, wherein an automation embodiment is presented for the early and multi-level diagnosis of dysplastic or cancer cells.

Isolation of Cell Membrane Ghosts

First, a sample of exfoliative cells is obtained from a patient. The sample contains approximately tens of millions of cells. This exfoliative cell population is washed in phosphate buffered saline at pH 7.0. A robotics device can be used to perform these assays. This assay is based upon cell and cell membrane, and nuclei sorting achieved by use of magnetic beads coated with antibody specific to a surface protein expressed on each analyte and subsequent detection of pathologic targets by CMSA or MACMSA. To achieve this, the entire cell population must be separated or sorted into subpopulations of cells or cell components of interest for analysis. These would include the pathologic cells themselves or cells that may be in the host range of a pathologic infectious virus or other organism.

In the exfoliative cell assay, the entire exfoliative cell population is captured on magnetic beads coated with antibody to a universal surface marker to initiate isolation of all nuclei in the sample. One embodiment uses the antibody, IgG anti-β2 microglobulin. Specific selection of the total cell population and lysis by complement addition, facilitates subsequent compartmentalization of nuclei and other cellular components for farther analysis for the presence of the pathologic cell or other targets.

Automation of exfoliative cell lysis (normal and precancerous cells) is based on the complement fixation of a universal cell antigen that is present in normal and abnormal cells. The marker used is the β2 microglobulin which associates with the Class I histocompatibility surface proteins on most all cells. For cells without this marker another surface marker can be used in conjuction to lyse the cancerous pathologic cell. Upon reaction of the monoclonal IgG anti-β2 microglobulin with the exfoliative cell sample, surface antigen/antibody complexes form, fix complement, and ultimately lyse all the cells in the sample releasing nuclei and cytoplasm for compartmentalization.

Addition of anti-β2 microglobulin to the bead causes the attachment of all cells in the sample, and in the presence of fresh guinea pig complement and cofactors for complement lysis, results in lysis of the exfoliative cells and release of cell contents. The cell contents, the flow through, are collected for further analyte (nucleus and cytoplasm) compartmentalization and target analysis.

The cell membrane ghosts attached to the anti-β2 microglobulin coated magnetic beads are washed and remain attached for further analysis. This also removes all ICPs generated by the cell lysis procedure. The cell membrane ghosts can be analyzed for the surface protein markers expressed in late dysplasia and early neoplasia (CIN III or HSIL) and advanced metastatic tumors listed in Table III (multiplex panel B).

Alternatively, another embodiment calls for the cells to be sorted at this first step by using cell surface protein markers expressed in late dysplasia and early neoplasia (CIN III or HSIL) and advanced metastatic tumors listed in Table III (multiplex panel B).

Isolation of Target Nuclei

The lysate containing intact nuclei, cell membrane ghosts, and cytoplasm from all cells present are mixed with mixtures of magnetic beads. Each magnetic beads grouping is coated with a single IgG monoclonal antibody or antibodies to an early dysplasia marker in panel A, thereby producing a magnetic bead cocktail. This permits the attachment of a pathogenic or target nucleus to the magnetic bead to permit sorting and isolation. The flow-through material, such as normal nuclei and the cytoplasm, are saved and compartmentalized for further analyte separation and analysis. The pathogenic nuclei retained represent all the dysplastic cells present and none of the normal cell nuclei.

The bead-nucleus complex is then washed thoroughly to eliminate all cytoplasmic remains, all normal nuclei and all complement present, including all ICPs produced. IgG anti-nuclear membrane markers for dysplasia in panel A (see Table II) are secondarily added to the bead bound dysplastic nuclei to saturate the nuclear membrane surface marker (panel A) sites on the pathologic nucleus.

Next, fresh immune complement is added, fixed, and activated by the surface-antigen/antibody complexes and eventually proceed to produce the ICPs. Production of these ICPs is directly related to the presence of the panel A dysplastic markers on the pathologic nuclei isolated.

Isolation of Target Cytoplasmic Proteins

The cytoplasmic proteins expressed in the dysplastic state, which are also part of the flow-through supernate can be removed from the cytoplasm using antibody coated magnetic beads specific to protein markers present in Table IV (multiplex panel C). The beads can then be assayed for the protein and quantification using CMSA or more correctly MACMSA.

Isolation of mRNA and DNA Species in the Nucleoplasm from the Target Nuclei

The nucleoplasm from the target lysed nuclei contains nucleoproteins and nucleic acids, DNA and RNA. The sample is treated by any method known by those skilled in the art that will denature and precipitate nucleases and other proteins such as SDS/KCL or proteinase K treatment, leaving the cellular DNA and RNA in solution.

At this point any Haystack Processing technology can be used to selectively directly detect the presence of mRNA species specific for the nuclear membrane, dysplastic marker, the cell surface membrane dysplastic marker, and the neoplastic cell surface markers.

The DNA and RNA are differentially removed from the deproteinated nuclear lysate by attachment to magnetic beads. The mRNA is selectively removed by interaction of the lysate with a poly dT coated magnetic bead which has an affinity for the poly A 3' mRNA regions of mRNA. The DNA is selectively removed by interaction of the lysate with a net positively charged magnetic bead surface with affinity for the highly negatively charged DNA molecule.

TPA Analysis of mRNA with the RP-TFO

Markers for analysis are presented in Table V and mRNA RP-TFO TPA analysis of the sample for the target mRNA species is depicted in FIGS. 5A, 5B and 6.

The following steps represent mRNA RP-TFO analysis, as presented in FIG. 6.

STEP I: At this point, the mRNA is tethered to the poly dT coated magnetic bead. The bead, after washing, is transferred to another well where the mRNA is dissociated using heat, alkali, or any other method.

STEP II: Hybridize the nucleic acid in solution specific for the mRNA molecules of the panel markers (see all panels, A, B, and C) with a series of RP-TFOs (Reverse Phase-Triplex Forming Oligonucleotides) covering all mRNA species in the marker panel chosen for testing. The RP-TFO possesses an affinity molecule, for example, a primary amine, that binds to a n-oxysuccinimide coated magnetic bead. This is a capture reverse polarity oligonucleatide.

STEP III: Next a magnetic bead coated with n-oxysuccinimide, or any other affinity molecule, captures the target mRNAs through the primary amine conjugated RP-TFO and results in covalent bond attachment of the PNAS.

STEP IV: Wash to remove non-specific material

STEP V: A single stranded 3'→5' nuclease may be added to degrade any non-specific mRNA remaining and specific mRNA from the poly A 3' end up to the RP-TFO anchor/attachment site. This step is optional and will reduce non-specific background signal.

STEP VI: A reporter probe is designed and hybridized to the 5' end of the mRNA target to form a duplex. Alternatively, in another embodiment, another RP-TFO can be used. Preferably, there is availability of an 11 mer poly rich region on the 5' end of the target mRNA.

This RP-TFO (reporter) carries an immunogenic epitope, which in this embodiment is biotin, but may be any immunogen or other epitope that fixes and activates complement. Any antigen/antibody pair can be used as well as any other molecule that will fix complement (biotin and IgG anti-biotin).

STEP VII: Wash the magnetic beads to remove non-bound reporter probes.
STEP VIII: Perform MACMSA employing any method for C3a assay to indicate the presence of the reporter probe associated in the structure containing the epitope.

TPA Analysis of DNA with the RP-TFO

The assay of DNA reflects targets of the nature presented in Table V. At this point, the genomic DNA is attached to a positively charged magnetic bead.

STEP I: The DNA coated magnetic bead is treated by any method known to dissociate it from the bead.
STEP II: The DNA is then heated to 40°–50° C. to allow the DNA to breathe and allow the RP-TFO to compete for the Crick (polypyrimidine) strand of the target.
STEP III: Add two RP-TFOs with an affinity capture molecule on one or both. Two RP-TFOs are preferred, one specific for a site upstream from the target and one specific for a site downstream from the target. Another magnetic bead is added with a surface coating that will bind the affinity molecule on the capture RP-TFO.
The modified purine bases in the RP-TFO will allow the RP-TFOs (2) to displace the Watson (purine) strand of the target thereby separating the Watson and Crick strands of the target in order to accommodate binding of the epitope substituted reporter probe (forming a duplex with either strand).

STEP IV: Wash to remove unbound RP-TFOs

STEP V: Add a reporter probe possessing an antigenic epitope to bind and form a duplex with either the Watson or Crick strands of the target (an RP-TFO may also be used).

STEP VI: Wash to remove unbound reporter probe.

STEP VII: Perform MACMSA as previously described in this document.

STEP VIII: Assay for C3a peptide production by any method known to those skilled in the art to confirm target presence.

Another embodiment calls for a biotin labeled reporter probe exposed to an IgG anti-biotin alkaline phosphatase polymer conjugate and use of a chemiluminescent substrate (1,2-Dioxetane) to detect the target.

EXAMPLE 2

The CMSA and MACMSA Diagnostic Assay for Carcinogens

The Detection of Aspergillus Species and the Mycotoxin Aflatoxin B1 (AFB1)

Aflatoxins are highly toxic and carcinogenic factors produced by mold contamination of soil-contacted foodstuffs such as peanuts and tobacco. They are usually produced by *Aspergillus flavus* and *Aspergillus parasiticus* and have been characterized as highly unsaturated molecules with a coumarin nucleus.

Aflatoxin B1 and G1 are the parent compounds and are potent carcinogens and have been shown to exert their carcinogenic effect by interaction with cellular nucleic acids. Aflatoxin B1 has been shown to suppress DNA, RNA and protein synthesis in rat liver cells. These mycotoxins, upon activation have been also shown to mutate both the p53 tumor suppressor gene as well as the K-ras genes. These mutations, generally guanine and cytosine transitions, implicate these mycotoxins as the causal agent in many human cancers, such as breast, colon, lung, pancreatic and others.

The mechanism of aflatoxin B1 reaction is through the formation of DNA adducts supporting the active mode of transport of extracellular toxin into eukaryotic cells, probably mediated by its lipid nature. Processes and strategies are continually being developed that will reduce the amount of aflatoxin in the consumed food or tobacco product; however, the inability to sensitively detect very low levels of mycotoxin prove the limiting factor in attempts to improve the safety for consumption of the ingested foodstuff.

Currently, assays for AFB1 are accomplished by chromatography, including high-pressure liquid chromatography (HPLC), reversed-phase liquid chromatography, thin-layer chromatography, adsorption chromatography, immunoaffinity chromatography, gas chromatography; enzyme-linked immunoadsorbent assay, fluorescent immunoassay, radioimmunoassay; spectroscopy, including mass spectroscopy, infrared spectroscopy, raman spectroscopy, packed-cell fluorescent spectroscopy; polymerase chain reaction (PCR), supercritical fluid extraction, bioluminescence, chemical luminescence, and combinations thereof. Fluorescent immunoassay is a presently preferred best mode for assaying for aflatoxin on tobacco achieving a lower sensitivity limit of only 3 parts per billion.

The aflatoxin B1 presence in tobacco provides a major health risk for users. Attempts have been made to reduce and limit its presence and have been met with strong criticism due to the inability to determine its presence with high sensitivity. Currently, FDA does not regulate AFB1 levels but does place limits of mold infection in raw tobacco to 300 parts per billion. With the knowledge that production of a single guanine or cytosine transition can predispose an individual to cancer the burden is upon diagnostic technology to sensitively detect the presence of aflatoxin B1 at much lower levels than is currently attainable. This increased sensitivity coupled with an effective tobacco treatment process to eliminate aflatoxin B1 can result in production of a tobacco product with much reduced risk of cancer production, a "safe" tobacco.

MACMSA requires the presence of an antigenic epitope on the carcinogen molecule and a monoclonal antibody specific to this epitope, both currently available for the AFBI molecule. This interaction (antigen/antibody complex) fixes and activates complement, and the activation is amplified by the presence of a lipid substrate, in this case, the sensitized RBC stroma. Complement fixation and activation will be monitored by C3a peptide production and its quantification. This involves the classical complement fixation pathway.

Similarly, the presence of Aspergillus species organism producing the AFB1 toxin can be detected in very low numbers in raw tobacco early in its processing. This is accomplished by CMSA and involves the alternate complement fixation pathway. The interaction of the mold's cell surface polysaccharides and lipopolysaccharides with complement Factor B, Factor D, and properdin activates the alternate complement pathway. Again complement activation occurs and will be monitored by C3a peptide production and quantification.

Utilizing CMSA and MACMSA, one can configure sensitive assays to follow the tobacco from its start through each stage of its processing and resulting in the production of a tobacco/end product that is essentially devoid of AFB1. Table VI presents a diagnostic scheme for Aspergillus species assay and soluble AFB1 assay through the tobacco processing procedure.

The following are the steps that comprise the quantitative assay for the organism that is present that produces the toxin. Any toxin producing organism known can be similarly detected.

Quantitative and Automated Raw Tobacco Assay for Aspergillus Species Organisms: C3a Sandwich Elisa STEP I: Prepare a batch homogenate of the sample for testing in buffer and centrifuge and remove the supernate STEP II: Add magnetic beads coated with a material specific for target, such as fungal cell wall attachment, as opposed to other microbes (differential binding of intact fungi) and mix STEP III: Wash STEP IV: Add fresh guinea pig complement and mix to activate the alternate pathway STEP V: Incubate at room temperature STEP VI: Flow through supernate containing any C3a peptides generated is added to magnetic beads coated with the IgG anti C3a capture monoclonal antibody STEP VII: Wash STEP VIII: Add IgG anti-C3a reporter monoclonal antibody conjugated with Alkaline phosphatase polymer and mix STEP IX: Wash STEP X: Detect, for example by adding the chemiluminescent a 1,2-Dioxetane substrate and generate stable light STEP XI: Quantify light produced The following are the steps that comprise the sensitive assay for the detection of the soluble AFB1 aflatoxin.

It is important to herein note that any toxin or carcinogen known to man can be similarly assayed, such as the most widely studied and suspected environmental carcinogens in lung cancer: polycyclic aromatic hydrocarbons (PAHs) including benzo(a)pyrene (BzP) and 4-(methylnitrosoamino)-1-(3-pyridyl)-1-butanone (NNK), along with the AFB1. The sole requirements are that the carcinogen possesses an immunogenic epitope and that a monoclonal or polyclonal antibody is available for use that has specificity for it. Interestingly, all these and other carcinogens and teratogens form adducts with specific DNA bases, a major factor exploited to allow its sensitive extraction and isolation from solution in vitro. Furthermore, all the above hydrocarbons are proven to cause specific mutations to the p53 tumor suppressor and K-ras genes.

Quantitative and Automated Tobacco Processing Assay for Soluble AFB1: Capture Strategy One-DNA Adduct Formation STEP I: Prepare batch homogenate of sample for testing in buffer and centrifuge and remove the supernate STEP II: Add magnetic beads coated with poly G•poly C duplex DNA (stable duplex) to allow adduct formation by soluble AFB1 molecules STEP III: Incubate at conditions favorable to formation of the adduct to bind soluble AFB1 to the GC duplex on the magnetic beads STEP IV: Wash to remove non-specific material STEP V: Add sensitized RBC stroma (sensitized with antibody pair: IgG anti Rh-IgG anti AFB1)

STEP VI: Incubate at conditions favorable to formation of the AFB1/anti AFB1 complex Step VII: Add fresh guinea pig complement and incubate at room temperature to allow production of C3a peptides.

STEP VIII: Flow through supernate containing any C3a peptides generated is added to magnetic beads coated with IgG anti C3a capture monoclonal antibody and mixed STEP IX: Wash to remove non-specific materials STEP X: Add IgG anti C3a reporter monoclonal antibody conjugated with alkaline phosphatase polymer and mix STEP XI: Wash to remove unbound reporter molecules STEP XII: Add a chemiluminescent substrate (a 1,2-Dioxetane)

STEP XIII: Measure light produced.

Quantitative and Automated Tobacco Processing Assay for Soluble AFB1: Capture Strategy Two-Affinity Molecule Association STEP I: Prepare batch homogenate of sample for testing in buffer and centrifuge and remove the supernate STEP II: Add magnetic beads coated with a material (lipophilic or other) that binds to AFB1

STEP III: Add sensitized RBC stroma (sensitized with antibody pair-IgG anti Rh-IgG anti AFB1)

STEP IV: Incubate at conditions favorable to formation of the AFB1/anti AFB1 complex STEP V: Add fresh guinea pig complement and incubate at room temperature to allow production of C3a peptides STEP VI: Flow through supernate containing any C3a peptides generated is added to magnetic beads coated with IgG anti C3a capture monoclonal antibody and mixed STEP VII: Wash to remove non-specific material STEP VIII: Add IgG anti C3a reporter monoclonal antibody conjugated with Alkaline phosphatase polymer and mix.

STEP IX: Wash to remove unbound reporter probe.

STEP X: Add the chemiluminescent substrate, a 1,2-Dioxetane.

STEP XI: Quantify light produced.

Quantitative and Automated Tobacco Processing Assay for Soluble AFB1: Capture and Assay Strategy Three-Sensitized RBC Lysis (Sensitized with the Ab Pair IgG Anti Rh-IgG Anti AFB1)

STEP I: Prepare batch homogenate of sample for testing in buffer

STEP II: Remove particulate material by filtration through a membrane, preferably using a filter system that is gravity driven STEP III: Add RBC sensitized cells (anti IgG anti Rh-IgG anti AFB1) to the clear filtrate STEP IV: Add guinea pig complement to lyse the RBCs.

STEP V: Monitor RBC lysis spectrophotometrically (hemoglobin release)

This assay may be of value in the early processing steps where AFB1 molecules range in the trillions.

EXAMPLE 3

Methods are herein presented to achieve early diagnosis of HIV infection allowing sorting and multi-level analysis of the virus containing target cell without interference from normal cells in the sample. No limit exists in the size of the sample that can be tested thereby assuring the ultimate sensitivity of the assay.

It is understood by those skilled in the art, that HIV has many cell types in its host range, including CD4 expressing T-cells, B-cells, and monocytes. Current thought is that the cell subset that is infected can provide valuable information for staging of the disease and design of treatment modalities.

STM and CMSA offer the capability for separate isolation of all the CD4 expressing T-cells, separate isolation of all B-cells, and separate isolation of all monocytes, by using magnetic beads coated with cell subset specific monoclonal antibodies, to achieve separation of non-HIV susceptible cell types and compartmentalization of HIV susceptible cell subsets.

This next step involves cell subset analysis by first, separating the component parts of each cell subset as described, herein, and next using the monoclonal antibodies to the markers of infection listed in Table VIII to assess the presence of the virus and the infectious state.

STM and CMSA analyses for HIV and other virus infections provide high specificity due to their ability to confirm the diagnostic result on multiple levels and provide high sensitivity due to their ability to screen a very large population of normal cells for low numbers of infected cells. In the STM CMSA processes normal cells are transparent to the assay and only the pathologic cell or component part resulting from the infection will generate a signal.

Upon infection of a normal cell by the HIV virus, a surface cell membrane HIV specific antigen and other markers are expressed in the infected cell and are not expressed in the normal nucleated cells of the peripheral blood. Isolation of a very large number of peripheral blood nucleated cells (PBNCs) and use of monoclonal antibody specific to this surface HIV marker expressed during cellular HIV infection in conjunction with the use of magnetic beads permits the selective identification and detection via CMSA of few pathologic target cells without the interference or high background signal generated by working with the entire population of white cells or with the cellular contents from normal cells. Signal amplification strategies are employed that do not produce non-specific signal known to be present in currently used enzyme systems.

This embodiment is also useful in monitoring protease inhibitor therapy in AIDS patients and supports sensitivities down to low infectious and other target number. In this embodiment, clearance of HV infected T-cells and other cells from the PBNC pool can be assayed and monitored. Other embodiments can detect the mRNA specific for any essential HIV replicative proteins down to low molecule numbers. For example, a single mRNA molecule specific for a tumor protein could trigger tens of thousands of identifiable signals.

The three categories or stages in the HIV disease time-course are presented in Table VII. By inspection of Tables VII and Table VIII, one can see a clear relationship between the stage in the infectious time-course and the types and locations along this time-course where these can be found. With this information, methods and compositions of the present invention can be used to produce diagnostic assays to screen for the presence of these markers on any type of specimen at any given stage of the entire infectious time-course, with emphasis on those markers that uniquely appear at given time in the course of the disease. Table VIII provides the target and its location site.

Use of this information and the methods presented herein, NTE, STM, CMSA, MACMSA, RP-TFO mRNA TPA, RP-TFO DNA TPA and use of these methods with robotics and magnetic beads in a automated format will result in highly specific and sensitive HIV diagnostic assay design and instrumentation.

EXAMPLE 4

Figure 4:
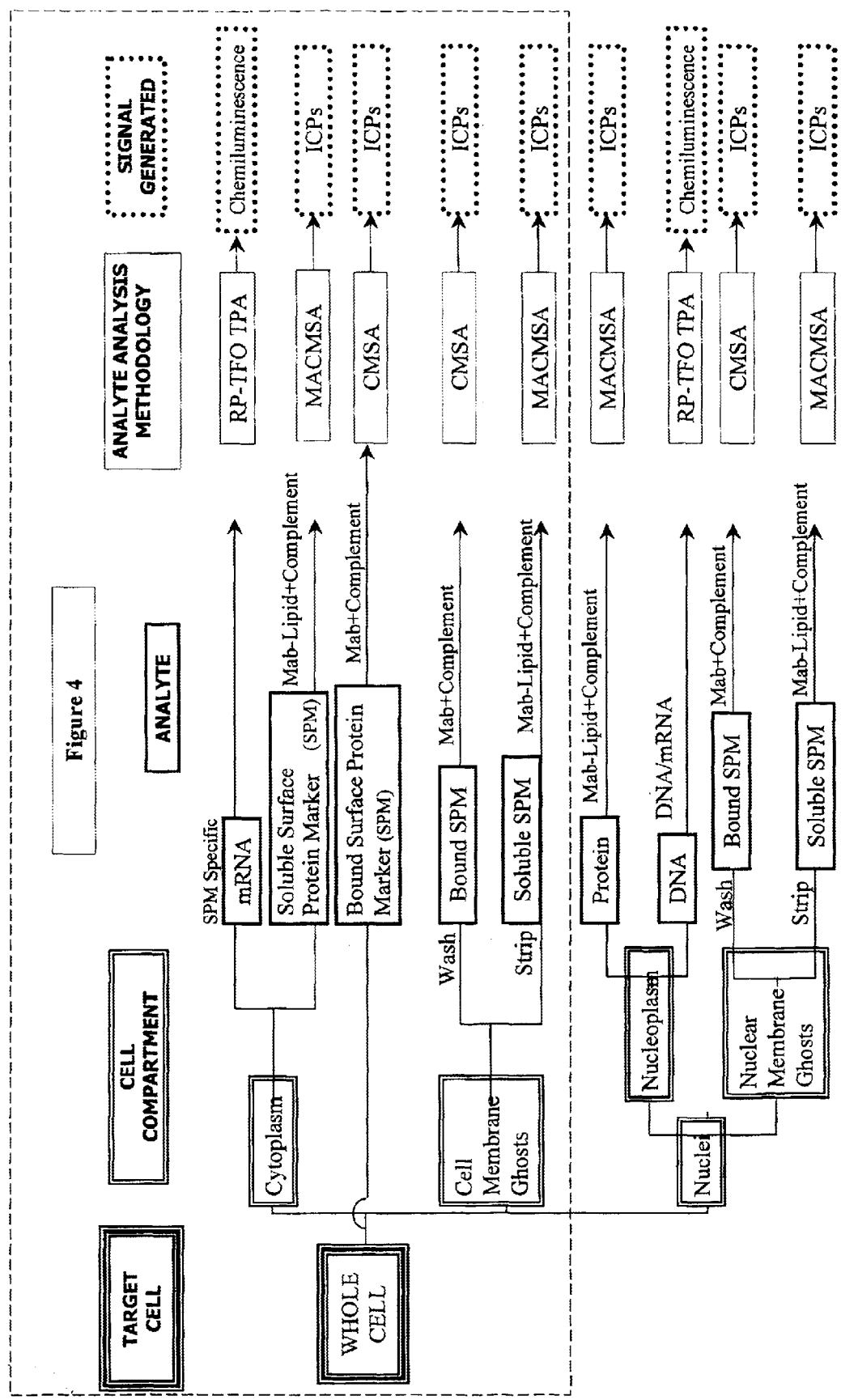

In this embodiment, depicted in FIG. 4, a few metastatic cells can be identified in a lymph node or residual disease can be determined in a tumor biopsy or FNA (fine needle aspirate) post-treatment. The node or cell mass for inspection is treated with collagenase to separate all individual cells without stripping off their surface membrane proteins (markers) that are characteristic of advanced neoplasia and these are specific to each type of neoplasia or in common in small disease clusters. Lymph nodes can be similarly disaggregated and screened for the presence of even a few metastatic cancer cells. Numerous mechanical and chemical methods are available for tissue disaggregation and include any known to those skilled in the art.

The whole cell with the intact surface membrane protein marker unique to the cancer is exposed to one or more monoclonal antibodies specific for the suspect tumor, or to a multiplex battery of many monoclonal antibodies with ranging specificities to detect the existence of neoplastic cells without regard to the specific tumor type. The confirmatory section of the test involves the analysis for the presence of marker specific mRNA in the nucleoplasm using assays such as mRNA TPA RP-TFO, disclosed in U.S. patent application Ser. No. 09/443,633 to confirm the presence of a true cancer cell producing its surface membrane protein markers.

The mRNA confirmatory component of the STM CMSA assay can include mRNA RP-TFO TPA or any other mRNA assay. The multilevel analysis of the compartmentalized parts of the cancer marker-bearing cell will provide a diagnostic result with the highest levels of specificity and sensitivity.

EXAMPLE 5
Detection of Aberrant Prion Protein

The sensitivity of detection of aberrant prion protein can be increased by, one, improving isolation of all prion molecules normal and aberrant from a large specimen (plasma or other), and two, developing an assay process that will permit a single pathologic prion to produce an amplified signal that will support its detection.

The method of the present invention, STM MACMSA can achieve these goals and perform sorting of protein molecules as well as providing increased signal amplification to detect the pathologic form.

STM/Prion Sorting in Soluble Protein Samples

One embodiment of prion sorting in a protein sample can be achieved by attachment of a monoclonal antibody specific for the C-terminal end of the molecule to a magnetic bead. The magnetic beads are placed in a large volume solution such as plasma or brain biopsy extract or any other and mixed. The epitopes available for interaction on the C-terminal end of the prion molecule remain exposed in both the normal and aberrant prion molecule.

The magnetic beads are collected with a magnet and washed in buffer. All the prion present in the sample will be separated from all other soluble proteins. The C-terminal antibody will capture the normal and pathologic prions due to the continued accessibility of the epitopes of both forms even after the transition has occurred.

In this embodiment the prion sorted magnetic bead is treated with a monoclonal antibody available to the N-terminal end of the prion molecule (the β sheet isoform end) that is labeled with an alkaline phosphatase polymer or any label known to those skilled in the art. Both are incubated and washed in buffer.

The N-terminal end of the pathologic prion has undergone a transition from an α to a β sheet form. During this transition, epitopes, normally found on the N-terminal end are covered and new epitopes exposed.

Monoclonal antibodies specific for the N-terminal end of the pathologic prion are necessary for use in these sensitive diagnostic assay embodiments.

Next, the magnetic beads are exposed to a chemiluminescent substrate, such as the 1,2-Dioxetanes, which would be able to detect 0.01 attomoles quantities of alkaline phosphatase enzyme. Theoretically, supporting increased sensitivity than that achieved by prion precipitation by sodium phosphotungstate and time resolved fluorescence previously mentioned.

STM MACMSA Sensitive Detection of Pathologic Prions

Another embodiment of STM for pathologic prion detection calls for use of sensitized RBC stroma to remove the pathologic prion (not the normal prion) from a large sample. This can be achieved by attachment, as herein described, of a monoclonal antibody specific to the N-terminal end (β sheet isoform) of the pathologic prion, which will not interact with the normal prion.

The stroma and sample can be mixed, incubated, and separated by centrifugation. The $PrP^{sc}$ containing stroma is then washed and treated with fresh complement, resulting in production of C3a ICPs directly proportional in number to the number of the β sheet isoform prion molecules present.

Theoretically each pathologic prion in this embodiment will generate a minimum of 40,000 C3a peptides for analysis.

The C3a peptides can then be assayed by any method known to those skilled in the art.

Although automation of this embodiment is difficult, some possibilities involve the usage of magnetic beads coated, not only with monoclonal antibody to the β sheet isoform N-terminal end, but also coated with a lipid matrix to exploit the full amplification possible by the complement system.

The theoretical enhanced sensitivity of this detection methodology and MACMSA signal amplification should exceed that achieved by prion precipitation by sodium phosphotungstate and time resolved fluorescence previously discussed.

Direct Immunoerythrocyte Lysis by Plasma or Other Supernates

Another embodiment of STM and CMSA that would offer less sensitivity due to the lack of signal amplification, but would still provide an acceptably lower sensitivity screening method would be to mix the solution containing the β sheet pathologic prion isoform with immunoerythrocytes sensitized with an antibody specific to an exposed epitope on the N-terminal end of the pathologic prion. A large sample may be used. This mix is followed by the addition of fresh complement. Theoretically, a single pathologic prion could cause the lysis of a single sensitized RBC. A positive assay result would be detected as lysis of the sensitized RBCs and release of hemoglobin. The simplicity, cost effectiveness and ease of performance of the embodiment will define its value.

TABLE II

CANDIDATES FOR MULTIPLEX PANEL A

| | | | | RELATIVE EXTENT OF EXPRESSION IN PRE-NEOPLASIA & NEOPLASIA | | | | |
|---|---|---|---|---|---|---|---|---|
| DYSPLASTIC MARKER | SITE OR LOCATION | CHARACTERISTIC OF EXPRESSION | NORMAL EXFOLIATIVE TISSUE | CIN I HPV (LSIL) | CIN II (HSIL) | CIN III (HSIL) | CARCINOMA IN SITU | INVASIVE CARCINOMA |
| Ki-67 (MIB-1) Antigen | Nuclear Membrane | Increasing with Stage | NEG. | +1 | +2 | +3 | +3 | +4 |
| Cdc, MCM Antigen | Nuclear Membrane | Increasing with stage | NEG. | +1 | +2 | +3 | +4 | +4 |
| NMP (CvC-3) | Nuclear Membrane | Increasing with Stage | NEG. | +1 | +2 | +3 | +4 | +4 |
| c-myc | Nuclear Membrane | Increasing with stage | NEG. | NEG. | NEG. | +1 | +2 | +4 |
| ras P31 | Nuclear Membrane | Increasing with Stage | NEG. | NEG. | NEG. | +1 | +2 | +4 |
| HMGI(Y) | Nuclear Membrane | Increasing with stage | NEG. | +1 | +2 | +3 | +4 | +4 |
| PCNA | Nuclear Membrane | Increasing with stage | NEG. | +1 | +2 | +3 | +4 | +4 |
| Topoisomerase II Alpha | Nuclear Membrane | Increasing with stage | NEG. | +1 | +2 | +3 | +3 | +4 |
| Cyclin B | Nuclear Membrane | Decreasing with stage | NEG. | +4 | +2 | +2 | +2 | +2 |

TABLE III

CANDIDATES FOR MULTIPLEX PANEL B

| | | | | RELATIVE EXTENT OF EXPRESSION IN PRE-NEOPLASIA & NEOPLASIA | | | | |
|---|---|---|---|---|---|---|---|---|
| DYSPLASTIC MARKER | SITE OR LOCATION | CHARACTERISTIC OF EXPRESSION | NORMAL EXFOLIATIVE TISSUE | CIN I HPV (LSIL) | CIN II (HSIL) | CIN III (HSIL) | CARCINOMA IN SITU | INVASIVE CARCINOMA |
| ESA | Cell Surface | Increasing with Stage | NEG. | +1 | +2 | +3 | +4 | +4 |
| Keratin-19 | Cell Surface | Increasing with stage | NEG. | NEG. | +2 | +2 | Lack of correlation with grade | Lack of correlation with grade |
| CD3-ZETA | Cell Surface | Increasing with stage | NEG. | NEG. | NEG. | +2 | +4 | +4 |

TABLE III-continued

CANDIDATES FOR MULTIPLEX PANEL B

| DYSPLASTIC MARKER | SITE OR LOCATION | CHARACTERISTIC OF EXPRESSION | RELATIVE EXTENT OF EXPRESSION IN PRE-NEOPLASIA & NEOPLASIA | | | | | |
|---|---|---|---|---|---|---|---|---|
| | | | NORMAL EXFOLIATIVE TISSUE | CIN I HPV (LSIL) | CIN II (HSIL) | CIN III (HSIL) | CARCINOMA IN SITU | INVASIVE CARCINOMA |
| MCP | Cell Surface | Increasing with stage | NEG. | NEG. | NEG. | +2 | +4 | +4 |
| HPV-IF | Cell Surface | Increasing with stage | NEG. | ± | +1 | +2 | +4 | +4 |
| Keratin-14 | Cell Surface | Increasing with stage | NEG. | +1 | +2 | +3 | +4 | +4 |
| Keratin-17 | Cell Surface | Increasing with stage | NEG. | NEG. | +1 | +2 | +2 | +4 |

TABLE IV

CANDIDATES FOR MULTIPLEX PANEL C

| DYSPLASTIC MARKER | SITE OR LOCATION | CHARACTERISTIC OF EXPRESSION | RELATIVE EXTENT OF EXPRESSION IN PRE-NEOPLASIA & NEOPLASIA | | | | | |
|---|---|---|---|---|---|---|---|---|
| | | | NORMAL EXFOLIATIVE TISSUE | CIN I HPV (LSIL) | CIN II (HSIL) | CIN III (HSIL) | CARCINOMA IN SITU | INVASIVE CARCINOMA |
| Bcl-2 | Cytoplasm | Derepression & Increase with Stage | NEG. | +1 | +2 | +3 | +4 | +4 |
| GST Pi | Cytoplasm | Increasing with Stage | NEG. | ± | +1 | +2 | +3 | +4 |
| p150 | Cytoplasm | Decreasing with stage | NEG. | +4 | +2 | +1 | +1 | +1 |
| TdR Pase | Cytoplasm | Increasing with stage | NEG. | +1 | +2 | +3 | +4 | +4 |
| NADH | Cytoplasm | — | NEG. | NEG. | NEG. | +4 | NEG. | NEG. |

TABLE V

CANDIDATES FOR MULTIPLEX PANEL D

| DYSPLASTIC MARKER | SITE OR LOCATION | ASSAY TYPE | RELATIVE EXTENT OF EXPRESSION IN PRE-NEOPLASIA & NEOPLASIA | | | | | |
|---|---|---|---|---|---|---|---|---|
| | | | NORMAL EXFOLIATIVE TISSUE | CIN I HPV (LSIL) | CIN II (HSIL) | CIN III (HSIL) | CARCINOMA IN SITU | INVASIVE CARCINOMA |
| *Chlamydia trichomatis* Infection | Cryptic DNA Plasmids in Cytoplasm | DNA | NEG. | YES | YES | YES | YES | YES |
| HPV Infection | DNA integrative form or RNA in Cytoplasm | DNA | NEG. | YES | YES | YES | YES | YES |
| Inflammatory Cells | PMN Leucocyte DNA in Cytoplasm | DNA | NEG. | YES | YES | YES | YES | YES |
| *Candida albicans* | DNA in cytoplasm | DNA | NEG. | YES | YES | YES | YES | YES |
| *Chlamydia Trichomatis* Infection | Cryptic DNA Plasmids in Cytoplasm | mRNA | NEG. | YES | YES | YES | YES | YES |
| HPV Infection | DNA integrative form or RNA in Cytoplasm | mRNA | NEG. | YES | YES | YES | YES | YES |
| Inflammatory Cells | PMN Leucocyte DNA in Cytoplasm | mRNA | NEG. | YES | YES | YES | YES | YES |
| *Candida albicans* | DNA in cytoplasm | mRNA | NEG. | YES | YES | YES | YES | YES |

TABLE V-continued

CANDIDATES FOR MULTIPLEX PANEL D

RELATIVE EXTENT OF EXPRESSION IN PRE-NEOPLASIA & NEOPLASIA

| DYSPLASTIC MARKER | SITE OR LOCATION | ASSAY TYPE | NORMAL EXFOLIATIVE TISSUE | CIN I HPV (LSIL) | CIN II (HSIL) | CIN III (HSIL) | CARCINOMA IN SITU | INVASIVE CARCINOMA |
|---|---|---|---|---|---|---|---|---|
| Cyclin E | Nuclear Membrane | mRNA | NEG. | YES | YES | YES | YES | YES |

TABLE VI

| TEST MATERIAL | RAW TOBACCO | EACH PROCESS STEP | QC VOLITILIZATION TESTING |
|---|---|---|---|
| ANALYTE | ASPERGILLUS SP. ASSAY | SOLUBLE AFB1 | SOLUBLE AFB1 | SOLUBLE AFB1 |
| DIAGNOSTIC PROCESS | CMSA Alternate Complement Fixation Pathway | MACMSA Classical Complement Fixation Pathway | MACMSA Classical Complement Fixation Pathway | MACMSA Classical Complement Fixation Pathway |
| THEORETIC SENSITIVITY LEVELS | FEW MICROORGANISMS (1 OR MORE) | FEW MOLECULES (1000 OR MORE) | FEW MOLECULES (1000 OR MORE) | FEW MOLECULES (1000 OR MORE) |
| VOLUME OF BATCH ALIQUOT TESTED | NO LIMITATION | NO LIMITATION | NO LIMITATION | NO LIMITATION |
| NON-SPECIFIC SIGNAL BACKGROUND | NONE | NONE | NONE | NONE |

TABLE VII

Consensus Time-Course of HIV Infection

Time Zero Infection → Seroconversion (HIV p24 Ag/Ab)(CDC System) → 6 months → 8 years → 12 years

| CDC | CATEGORY 1 | | | CATEGORY 2 | | CATEGORY 3 | |
|---|---|---|---|---|---|---|---|
| CD4 Count | ≥500 cells/mm³ | | | 200–499 cells/mm³ | | <200 cells/mm³ | |
| Clinical Categories | CATEGORY A | | | CATEGORY B | | CATEGORY C | |
| Clinical Characterization | • Persistent Generalized Lymphadenopathy<br>• Primary HIV Infection<br>• Asymptomatic Acute Primary Infection | | | • Defect in Cell Mediated Immunity<br>• (ARC)<br>• Not A or C Conditions | | • (AIDS)<br>• Indicator Conditions (disease) | |
| | No Antibody or Virus Isolation (not currently used) | Asymptomatic (60%) | Chronic Lymphadenopathy | T Helper Depletion | Delayed Hypersensitivity | Thrush | O.I. Opportunistic Infections |
| Walter Reed | ←WR0→ | WR1 | WR2 | WR3 | WR4 | WR5 | WR6 |
| CD4 Count cells/mm³ | >400 | >400 | >400 | <400 | <400 | <400 | <400 |
| Stage Progression | | equal | | longer | | very rapid | |

↑ Seroconversion(Walter Reed System)

TABLE VIII

| PROTEIN MARKER | CELL SURFACE MEMBRANE | SURFACE CELL MEMBRANE GHOST | NUCLEOPLASM | CYTOPLASM | VIRUS |
|---|---|---|---|---|---|
| env gp120 (virion) | ✓ | ✓ | DNA or RNA | ✓ | ✓ |
| V3 fusion peptide of gp41 | ✓ | ✓ | | | ✓ |
| V3 fusion peptide of gp120 | ✓ | ✓ | | | ✓ |
| Reverse Transcriptase (RT) | | | ✓ | ✓ | ✓ |
| *Integrase (IN) | | | ✓ | ✓ | ✓ |
| PR (Protease) | | | ✓ | ✓ | ✓ |
| Linear DNA ē 2 LTR regions | | | Linear DNA ✓ | ✓ | ✓ |
| Circular DNA ē 1 or 2 LTR regions | | | Circular DNA ✓ | no | ✓ |
| tat | | | ✓ | ✓ | |
| | gp120 ✓ | gp41 ✓ | | gp160 ✓ | |
| vif | | | | ✓ | |
| vpu | | | | ✓ | |
| vpr 100/virus partiele | | | | ✓ | |
| gag (pr55) | ✓ | ✓ | | ✓ precursor | ✓ final |
| gag-pol (pr160) | ✓ | ✓ | | ✓ precursor | ✓ final |
| | | | | mRNA ✓ | |
| | | | | mRNA ✓ | |
| Packaging signal | ✓ | ✓ | | ✓ | |
| gp160 | | | ✓ | ✓ | |
| gp120 | ✓ | ✓ | ✓ | | |
| gp41 | ✓ | ✓ | ✓ | | |
| MA gag protein (matrix) | | | ✓ | | ✓ |
| CA gag protein (core) | | | ✓ | | ✓ |
| NC gag protein (nucleocapsid) | ✓ | ✓ | ✓ | | ✓ |
| Genomic viral RNA | | | ✓ | ✓ | |

*essential and important

REFERENCES

1. Koss, L. G., The Papanicolaou test for cervical cancer detection. A triumph and a tragedy. JAMA February 1989; 261(5):737–43.
2. Torres F X, Mackowiak P F, Brown R D, Linden M D, and Zarbo R J. Comparison of two methods of mechanical disaggregation of scirrhous breast adenocarcinomas for DNA flow cytometric analysis of whole cells. J. Clin. Pathol. January 1995; 103(1):8–13.
3. Warzynski M J, Podguski A E, Boldt D M. Otto R N. An automated method to prepare cell suspensions from human biopsy samples for immunophenotyping by flow cytometry. Am. J. Clin. Pathol. June 1990; 93(1);104–8.
4. Ottesen G L, Christensen I J, Larsen J K, Hansen B, Andersen J A. Tissue disaggregation for flow cytometric DNA analysis: comparison of fine-needle aspiration and an automated mechanical procedure. Cytometry Mar. 15, 1996; 26(1):65–8
5. Brockhoff G, Fleischmann S, Meier A, Wachs F P, Hofstaedter F, Knuechel R. Use of a mechanical dissociation device to improve standardization of flow cytometric cytokeratin DNA measurement of colon carcinomas. Cytometry Aug. 15, 1999; 38(4):184–91
6. Baer P C, Nockher W A, Hasse W, Scherberich J E. Isolation of proximal and distal tubule cells from human kidney by immunomagnetic separation. Technical note. Kidney Int. 1997 Now;52(5):1321–31
7. Rogler G, Hausmann M, Vogl D, Aschenbrenner E, Andus T, Falk W, Andreesen R, Scholmerich J, Gross V. Isolation and phenotypic characterization of colonic macrophages. Clin. Exp. Immunol. May 1998;112(2):205–15
8. Kedar E, Ikejiri B L, Bonnard G D, Herberman R B. A rapid technique for isolation of viable tumor cells from solid tumors: use of the tumor cells for induction and measurement of cell-mediated cytotoxic responses. Eur. J. Cancer Clin. Oncol. October 1982; 18(10):991–1000
9. Wilson J K, Pretlow T G, Zaremba J L, Brattain M G. Heterogeneity among preparations of crude trypsin used to disaggregate the human tonsil. Immunology January 1976;30(1):157–60
10. Hemstreet G P 3rd, Enoch P G, Pretlow T G 2d. Tissue disaggregation of human renal cell carcinoma with further isopyknic and isokinetic gradient purification. Cancer Res. April 1980;40(4):043–9
11. Rasey J S, Nelson N J. Effect of tumor disaggregation on results of in vitro cell survival assay after in vivo treatment of the EMT-6 tumor: x-rays, cyclophosphamide, and bleomycin. In Vitro July 1980;16(7):547–53
12. Speicher D W, McCarl R L. Evaluation of a proteolytic enzyme mixture from crude trypsins in tissue disaggregation. In Vitro October 1978;14(10):849–53
13. Brendler-Schwaab S Y, Herbold B A. A new method for the enrichment of single renal proximal tubular cells and their first use in the comet assay. Mutat Res Sep. 18, 1997;393(1–2):175–8
14. Besch G J, Wolberg W H, Gilchrist K W, Voelkel J G, Gould M N. A comparison of methods for the production of monodispersed cell suspensions from human primary breast carcinomas. Breast Cancer Res Treat 1983;3(1):15–22
15. Singh, N P. A rapid method for the preparation of single cell suspensions from solid tissues. Cytometry Mar. 1, 1998; 31(3):229–32
16. Risberg B, Stal O, Eriksson L L, Hussein A. DNA flow cytometry on breast carcinomas: comparison of a detergent and an enzyme-detergent preparation method. Anal. Cell Pathol. Sep. 25, 1990; (5):287–95.
17. Risberg B, Stal O, Eriksson L L, Hussein A. DNA flow cytometry on breast carcinomas: comparison of a detergent and an enzyme-detergent preparation method. Anal. Cell Pathol. Sep. 25, 1990; (5):287–95.
18. Bronstein, I, Brooks, E, Voyta J C. 1,2-Dioxetanes: Novel Chemiluminescent Enzyme Substrates. Application to Immunoassays. J Bioluminescence & Chemiluminescence 1989 Vol.4: 99–111
19. Bruce, M E, Will R G, Ironside J W, et al. Transmissions to mice indicate that "new variant" CJD is caused by the BSE agent. Nature October 1997 Vol. 389:498
20. Safar, J, Wille, H, Itri, V, et al. Eight prion strains have PrPsc molecules with different conformations. Nature Medicine October 1998 Vol.4 (10):1157–1165

What is claimed:

1. A method for detection of one or more specific target analytes in a sample, comprising,
    a) providing a sample and treating said sample with at least one antibody specific to an antigenic marker on a target analyte for forming a complex that fixes at least one complement molecule;
    b) activating the complement cascade for producing at least one inactive complement peptide (ICP);
    c) amplifying said production of said ICP by employing at least one lipid membrane;
    d) measuring the presence of ICP; and
    e) detecting said target analyte wherein the quantity of ICP is directly proportional to the number of said target analyte in said sample.

2. The method of claim 1, wherein the target analyte is a cell.

3. The method of claim 1, wherein the target analyte is a nucleic acid.

4. The method of claim 1, wherein the complement cascade is the classical complement cascade.

5. The method of claim 1, wherein the complement cascade is the alternate complement cascade.

6. The method of claim 1, wherein the antibody comprises a pair of antibodies linked together.

7. The method of claim 1, wherein the ICP measured is C3a.

8. A method for detecting a carcinogen, comprising
    a) providing a sample and treating said sample with at least one antibody specific to an antigenic marker on a carcinogen for forming a complex that fixes at least one complement molecule;
    b) activating the complement cascade for producing at least one inactive complement peptide (ICP);
    c) amplifying said production of said ICP by employing at least one lipid membrane;
    d) measuring the presence of ICP; and
    e) detecting said carcinogen wherein the quantity of said ICP is directly proportional to the number of said carcinogen in said sample.

9. The method of claim 1, wherein the target analyte is a nucleic acid.

10. The method of claim 1, wherein the complement cascade is the classical complement cascade.

11. The method of claim 1, wherein the complement cascade is the alternate complement cascade.

12. A method for detecting a cancerous cell, comprising
    a) providing a sample and treating said sample with at least one antibody specific to an antigenic marker on a cancerous cell for forming a complex that fixes at least one complement molecule;
    b) activating the complement cascade for producing at least one inactive complement peptide (ICP);
    c) amplifying said production of said ICP by employing at least one lipid membrane;
    d) measuring the presence of ICP; and
    e) detecting said carcinogen wherein the quantity of said ICP is directly proportional to the number of said carcinogen in said sample.

* * * * *

UNITED STATES PATENT AND TRADEMARK OFFICE
CERTIFICATE OF CORRECTION

PATENT NO. : 6,709,829 B2
DATED : March 23, 2004
INVENTOR(S) : Elliot R. Ramberg It is certified that error appears in the above-identified patent and that said Letters Patent is hereby corrected as shown below:

<u>Columns 31 and 32,</u>
Table II, in the column entitled "Dysplastic Marker", last line, change "Cyclin B" to
-- Cyclin E --, Signed and Sealed this Thirtieth Day of November, 2004

JON W. DUDAS
*Director of the United States Patent and Trademark Office*